(12) United States Patent
Raghavan et al.

(10) Patent No.: US 9,553,465 B2
(45) Date of Patent: Jan. 24, 2017

(54) BATTERY MANAGEMENT BASED ON INTERNAL OPTICAL SENSING

(71) Applicant: Palo Alto Research Center Incorporated, Palo Alto, CA (US)

(72) Inventors: Ajay Raghavan, Mountain View, CA (US); Peter Kiesel, Palo Alto, CA (US); Alexander Lochbaum, Mountain View, CA (US); Bhaskar Saha, Union City, CA (US); Lars Wilko Sommer, Mountain View, CA (US); Tobias Staudt, Palo Alto, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 54 days.

(21) Appl. No.: 14/257,673

(22) Filed: Apr. 21, 2014

(65) Prior Publication Data

US 2015/0303723 A1    Oct. 22, 2015

(51) Int. Cl.
*H02J 7/00* (2006.01)
*G01N 33/00* (2006.01)
(Continued)

(52) U.S. Cl.
CPC .......... *H02J 7/0052* (2013.01); *G01N 21/7703* (2013.01); *G01N 33/0036* (2013.01);
(Continued)

(58) Field of Classification Search
CPC ........ H02J 7/0052; H02J 7/007; H02J 7/0031; G01N 21/7703; G01N 33/0036; G01N 2021/772; G01N 2021/7786; G01N 2021/7709; G01N 2021/7783; G01N 2021/0112; G01R 31/3679; G01R 31/3606; H01M 10/48; H01M 10/052; Y02E 60/122

See application file for complete search history.

(56) References Cited

U.S. PATENT DOCUMENTS 4,240,747 A  *  12/1980  Harmer ................. G01N 21/431
                                                        250/227.25
5,660,944 A  *   8/1997  Sprengel ................. H01M 2/12
                                                            429/90
(Continued)

FOREIGN PATENT DOCUMENTS

EP             2492989         10/2013
JP        63301470 A    *   12/1988
(Continued)

OTHER PUBLICATIONS

Koch et al., "Arrayed waveguide grating interrogator for fiber Bragg grating sensors: measurement and simulation", Applied Optics, vol. 51, No. 31, Nov. 1, 2012, pp. 7718-7723.
(Continued)

*Primary Examiner* — Naum B Levin
(74) *Attorney, Agent, or Firm* — Hollingsworth Davis, LLC

(57) ABSTRACT

A battery management system includes one or more fiber optic sensors configured to be disposed within an electrochemical battery. Each fiber optic sensor is capable of receiving input light and providing output light that varies based on the input light and an amount of free or dissolved gas present within the battery. A detector detects the output light and generates an electrical detector signal in response to the output light. Battery management circuitry determines the state of the battery based at least in part on the detector signal.

26 Claims, 13 Drawing Sheets

(51) Int. Cl.
*G01R 31/36* (2006.01)
*H01M 10/052* (2010.01)
*H01M 10/48* (2006.01)
*G01N 21/77* (2006.01)
*G01N 21/01* (2006.01)

(52) U.S. Cl.
CPC ..... *G01R 31/3606* (2013.01); *G01R 31/3679* (2013.01); *H01M 10/052* (2013.01); *H01M 10/48* (2013.01); *H02J 7/007* (2013.01); *H02J 7/0031* (2013.01); *G01N 2021/0112* (2013.01); *G01N 2021/772* (2013.01); *G01N 2021/7709* (2013.01); *G01N 2021/7783* (2013.01); *G01N 2021/7786* (2013.01); *Y02E 60/122* (2013.01)

(56) References Cited

U.S. PATENT DOCUMENTS

| | | | |
|---|---|---|---|
| 5,949,219 A | 9/1999 | Weiss | |
| 5,995,686 A | 11/1999 | Hamburger et al. | |
| 6,051,437 A * | 4/2000 | Luo | B82Y 15/00 422/82.05 |
| 6,265,100 B1 * | 7/2001 | Saaski | H01M 10/0431 429/161 |
| 6,285,807 B1 * | 9/2001 | Walt | G01N 21/8507 250/227.14 |
| 6,379,969 B1 * | 4/2002 | Mauze | G01N 21/6428 422/82.05 |
| 6,828,055 B2 * | 12/2004 | Kearl | H01M 8/0204 429/423 |
| 7,135,342 B2 * | 11/2006 | Colvin, Jr. | G01N 21/6428 422/82.05 |
| 7,155,075 B2 | 12/2006 | Rajendran et al. | |
| 7,263,246 B1 * | 8/2007 | Duan | G01N 21/552 385/12 |
| 7,306,951 B1 * | 12/2007 | Benson | G01N 21/783 422/83 |
| 7,310,153 B2 | 12/2007 | Kiesel et al. | |
| 7,315,667 B2 | 1/2008 | Kiesel et al. | |
| 7,433,552 B2 | 10/2008 | Kiesel | |
| 7,511,823 B2 | 3/2009 | Schultz et al. | |
| 7,522,786 B2 | 4/2009 | Kiesel et al. | |
| 7,589,312 B2 | 9/2009 | Kojima | |
| 7,695,970 B2 * | 4/2010 | Parnas | G01N 21/643 422/82.05 |
| 7,701,590 B2 | 4/2010 | Kiesel et al. | |
| 7,718,948 B2 | 5/2010 | Kiesel | |
| 7,766,544 B2 | 8/2010 | Shibuya et al. | |
| 8,097,352 B2 * | 1/2012 | Fuse | H01M 6/505 324/426 |
| 8,143,070 B2 * | 3/2012 | Tokhtuev | G01N 21/05 356/246 |
| 8,148,165 B2 * | 4/2012 | Nakano | G01N 21/80 422/50 |
| 8,241,911 B2 * | 8/2012 | Ascheman | G01N 21/274 136/290 |
| 8,268,493 B2 * | 9/2012 | Cetegen | G01K 11/003 429/400 |
| 8,437,582 B2 | 5/2013 | Kiesel | |
| 8,594,470 B2 | 11/2013 | Kiesel et al. | |
| 8,729,862 B2 * | 5/2014 | Yebka | H02J 7/0075 320/128 |
| 8,808,890 B2 * | 8/2014 | Fuse | H01M 10/0525 324/426 |
| 9,000,718 B2 * | 4/2015 | Park | B60L 3/0046 320/107 |
| 2004/0033004 A1 | 2/2004 | Welch et al. | |
| 2005/0026134 A1 * | 2/2005 | Miller | B01L 3/502746 506/14 |
| 2006/0045412 A1 | 3/2006 | Xiao et al. | |
| 2008/0231836 A1 * | 9/2008 | Curello | H01M 8/04201 356/72 |
| 2009/0027009 A1 | 1/2009 | Sivertsen | |
| 2009/0220189 A1 | 9/2009 | Kiesel | |
| 2009/0274849 A1 | 11/2009 | Scott et al. | |
| 2010/0032009 A1 | 2/2010 | Skryabin | |
| 2010/0247027 A1 | 9/2010 | Xia et al. | |
| 2012/0232354 A1 * | 9/2012 | Ecker | A61B 5/046 600/300 |
| 2012/0321242 A1 | 12/2012 | Schade et al. | |
| 2013/0071739 A1 * | 3/2013 | Tajima | B82Y 30/00 429/211 |
| 2013/0312947 A1 | 11/2013 | Bandhauer et al. | |
| 2013/0314094 A1 | 11/2013 | Farmer et al. | |
| 2013/0316198 A1 * | 11/2013 | Bandhauer | H01M 10/502 429/50 |
| 2014/0072836 A1 * | 3/2014 | Mills | C25B 1/04 429/8 |
| 2014/0092375 A1 | 4/2014 | Raghavan et al. | |
| 2014/0203783 A1 * | 7/2014 | Kiesel | H01M 10/42 320/134 |
| 2014/0272493 A1 * | 9/2014 | Evans | H01M 8/188 429/63 |
| 2014/0312828 A1 * | 10/2014 | Vo | H01M 10/4257 320/103 |
| 2014/0363747 A1 * | 12/2014 | Evans | H01M 8/188 429/409 |
| 2015/0214757 A1 * | 7/2015 | Zane | H02J 7/0021 320/107 |
| 2015/0255824 A1 * | 9/2015 | Evans | H01M 8/20 429/418 |

FOREIGN PATENT DOCUMENTS

| | | |
|---|---|---|
| JP | 2009059582 | 3/2009 |
| WO | WO2014026093 | 2/2014 |

OTHER PUBLICATIONS

Niewczas et al. "Performance Analysis of the Fiber Bragg Grating Interrogation System Based on an Arrayed Waveguide Grating", IEEE Transactions on Instrumentation and Measurement, vol. 53, No. 4, Aug. 2004, pp. 1192-1195.

Li et al., "Preliminary Investigation of an SOI-based Arrayed Waveguide Grating Demodulation Integration Microsystem" Scientific Reports, May 6, 2014, 6 pages.

File History for U.S. Appl. No. 13/630,660.

Cao-Paz et al., "A Multi-Point Sensor Based on Optical Fiber for the Measurement of Electrolyte Density in Lead-Acid Batteries", Sensors 2010, 10, pp. 2587-2608.

Corbellini et al., "Modified POF Sensor for Gaseous Hydrogen Fluoride Monitoring in the Presence of Ionizing Radiations", IEEE Transactions on Instrumentation and Measurement, vol. 61, No. 5, May 2012, pp. 1201-1208.

Grobnic et al., "Sapphire Fiber Bragg Grating Sensor Made Using Femtosecond Laser Radiation for Ultrahigh Temperature Applications", IEEE Photonics Technology Letters, vol. 16, No. 11, Nov. 2004, p. 2505-2507.

Haase, "Strain Sensors Based on Bragg Gratings", IMEKO 20th TC3, 3rd TC16 and 1st TC22 International Conference Cultivating Metrological Knowledge, Nov. 27, 2007, 8 pages.

Jansen et al., "Low-Cost Flexible Packaging for High-Power Li-Ion HEV Batteries", FreedomCar & Vehicle Technologies Office, Jun. 2004, 56 pages.

Juergens et al., "Performance Evaluation of Fiber Bragg Gratings at Elevated Temperatures", NASA, Jan. 2004, 14 pages.

Kersey et al., "Fiber Grating Sensors", Journal of Lightwave Technology, vol. 15, No. 8, Aug. 1997, pp. 1442-1463.

Klein et al., "Optimal Charging Strategies in Lithium-Ion Battery", 2011 American Control Conference, Jun. 29-Jul. 1, 2011, pp. 382-387.

Kumai et al., "Gas Generation Mechanism Due to Electrolyte Decomposition in Commercial Lithium-Ion Cell", Journal of Power Sources 81-82, 1999, pp. 715-719.

Lee et al., "In Situ Monitoring of Temperature Inside Lithium-Ion Batteries by Flexible Micro Temperature Sensors", Sensors 2011, 11, pp. 9942-9950.

(56) References Cited

OTHER PUBLICATIONS

Liang et al., "Highly Sensitive Fiber Bragg Grating Refractive Index Sensors", Applied Physics Letters, vol. 86, 2005, pp. 151122-1-151122-3.
Merzbacher et al., "Fiber Optic Sensors in Concrete Structures: A Review", Smart Mater. Struct., 5, 1996, pp. 196-280.
Pinson et al., Theory of SEI Formation in Rechargeable Batteries: Capacity Fade, Accelerated Aging and Lifetime Prediction, 223rd ECS Meeting, May 12-17, 2013, 29 pages.
Qi et al., "In Situ Observation of Strains During Lithiation of a Graphite Electrode", Journal of the Electrochemical Society, vol. 157 (6), 2010, pp. A741-A747.
Qin et al., "Specific Fluorescence Determination of Lithium Ion Based on 2-(2-hydroxyphenyl)benzoxazole", The Royal Society of Chemistry, 2001, pp. 1499-1501.
Rodrigues et al., "A Review of State-of-Charge Indication of Batteries by Means of A.C. Impedance Measurements", Journal of Power Sources, vol. 87, 2000, pp. 12-20.
Roth et al., "Thermal Abuse Performance of 18650 Li-Ion Cells", Sandia Report, Mar. 2004, pp. 1-139.
Sang et al., "Temperature-Insensitive Chemical Sensor Based on a Fiber Bragg Grating", Sensors and Actuators B 120, 2007, pp. 754-757.
Siegel et al., "Neutron Imaging of Lithium Concentration in FLP Pouch Cell Battery", Journal of the Electrochemical Society, 158 (6), 2011, 8 pages.
Smith et al., "Power and Thermal Characterization of a Lithium-Ion Battery Pack for Hybrid-Electric Vehicles", Journal of Power Sources 160, 2006, pp. 662-673.
Tang et al., "Measurement of Chloride-Ion Concentration with Long-Period Grating Technology", Smart Mater. Struct. vol. 16, 2007, pp. 665-672.
Van Steenkiste et al., "Strain and Temperature Measurement with Fiber Optic Sensors", 1997, 9 pages.
Wang et al., "Aging Effects to Solid Electrolyte Interface (SEI) Membrane Formation and the Performance Analysis of Lithium Ion Batteries", Int. J. Electrochem, Sci., 6, 2011, pp. 1014-1026.
U.S. Appl. No. 14/331,318, Jul. 15, 2014, Hegyi et al.
Chehura et al. "Temperature and strain discrimination using a single tilted fibre Bragg grating", Opt. Commun., vol. 275, No. 2, Jul. 2007, pp. 344-347.
Guan et al. "Simultaneous strain and temperature measurement using a single fibre Bragg grating", Electron. Lett.,vol. 36, No. 12, 2000, pp. 1018-1019.
Jin et al. "Geometric representation of errors in measurements of strain and temperature", Opt. Eng., vol. 36, No. 8, 1997, pp. 2272-2278.
Jin et al. "Simultaneous measurement of strain and temperature: error analysis". Opt. Eng .• vol. 36, No. 2, 1997. pp. 598-609.
Patrick et al. "Hybrid fiber Bragg grating/long period fiber grating sensor for strain/temperature discrimination", IEEE Photonics Technol. Lett., vol. 8, No. 9, 1996, pp. 1223-1225.
Rao: "In-fibre Bragg grating sensors", Meas. Sci. Technol., vol. 8, No. 4, Apr. 1997, pp. 355-375.
Reimers et al. "Electrochemical and in Situ X-Ray Diffraction Studies of Lithium Intercalation in Li x Co02", Journal of the Electrochemical Society, 139 (8),1992.
Saha et al. "Battery Data Set", NASA Ames Prognostics Data Repository, 2007, Available online: http://tLarc.nasa.gov/tech/dash/pcoe/prognostic-data-repository/.
Sethuraman et al. "Surface structural disordering in graphite upon lithium intercalation/deintercalation", Journal of Power Sources 195 (2010) 3655-3660.
Triollet et al. "Discriminated measures of strain and temperature in metallic specimen with embedded superimposed long and short fibre Bragg gratings", Meas. Sci. Technol., vol. 22, No. 1, Jan. 2011, pp. 015202.
Wang et al. "Simultaneous measurement of strain and temperature using dual-period fiber grating", Proc. SP!E, vol. 4579, 2001, pp. 265-268.
Wang et al. "Understanding Volume Change in Lithium-Ion Cells during Charging and Discharging Using in Situ Measurements", Journal of the Electrochemical Society, 154 (1), 2007.
Xu et al. "Discrimination between strain and temperature effects using dual-wavelength fibre grating sensors", Electron. Lett., vol. 30, No. 13, pp. 1085-1087, 1994.
Zhao et al. "Discrimination methods and demodulation techniques for fiber Bragg grating sensors", Opt. Lasers Eng., vol. 41, No. 1, pp. 1-18, Jan. 2004.
Zhou et al. "Simultaneous measurement for strain and temperature using fiber Bragg gratings and multimode fibers", Appl. Opt., vol. 47, No. 10, Apr. 2008, pp. 1668-1672.
File History for U.S. Appl. No. 14/242,853.
File History for EP App. No. 15174916.5 as retrieved from the EP Electronic File System on Aug. 5, 2016, 117 pages.
File History for EP App. No. 15162467.3 as retrieved from the EP Electronic File System on Aug. 5, 2016, 103 pages.

* cited by examiner

BATTERY MANAGEMENT BASED ON INTERNAL OPTICAL SENSING

STATEMENT REGARDING FEDERALLY SPONSORED RESEARCH AND DEVELOPMENT

This invention was made with government support under contract DE-AR0000274 awarded by ARPA-E (Advanced Research Projects Agency-Energy). The government has certain rights in the invention.

TECHNICAL FIELD

This application relates generally to techniques for monitoring and/or managing batteries. The application also relates to components, devices, systems, and methods pertaining to such techniques.

BACKGROUND

Battery management systems that rely on external cell performance parameters to determine state-of-charge (SOC) and/or state-of-health (SOH) result in conservative overdesign to manage the uncertainty in battery state-of-charge and battery degradation with aging. This reliance on conservative overdesign of batteries has affected the widespread adoption of clean technologies such as electric vehicles and power grid storage. Conservative overdesign of batteries arises in part because the battery state cannot be fully understood from external parameters alone.

SUMMARY

Embodiments disclosed herein are directed to battery management systems (BMS) and methods. The BMS includes one or more fiber optic sensors that are configured to be disposed within an electrochemical battery. Each fiber optic sensor is configured to receive input light and to provide output light that varies based on the amount of free or dissolved gas present within the battery. The BMS includes a light source configured to provide input light to the sensors. A detector is configured and arranged to detects the output light and to generate an electrical detector signal in response to the output light. Battery management circuitry determines the state of the battery based at least in part on the detector signal. The battery state determined can include the state of charge or state of health of the battery, for example.

Some embodiments involve a system for forming an electrochemical battery. The system includes one or more fiber optic sensors configured to be disposed within a case of the battery. Each fiber optic sensor is configured to receive input light and to provide output light that varies based on an amount of a gas present within the battery. A light source is configured to provide the input light to the fiber optic sensors. A detector detects output light from the sensors and generates an electrical signal in response to the output light. The system includes charging circuitry configured to charge the battery. Battery management circuitry provides feedback information to the charging circuit to control formation of the battery electrodes based at least in part on the detector signal.

Some embodiments involve a method of battery management that includes optically sensing within an electrochemical battery an amount of a free or dissolved gas present within the battery. An electrical signal is generated in response to the sensed amount of gas. The state of the battery is determined based at least in part on the signal. For example, the state of the battery may comprise a state of charge or state of health of the battery. Various optional processes may be implemented based on the battery state, such as controlling charging or discharging of the battery, or providing an indication of the battery state, e.g., normal operating state, overcharged, overdischarged, etc.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DESCRIPTION

Figure 1:
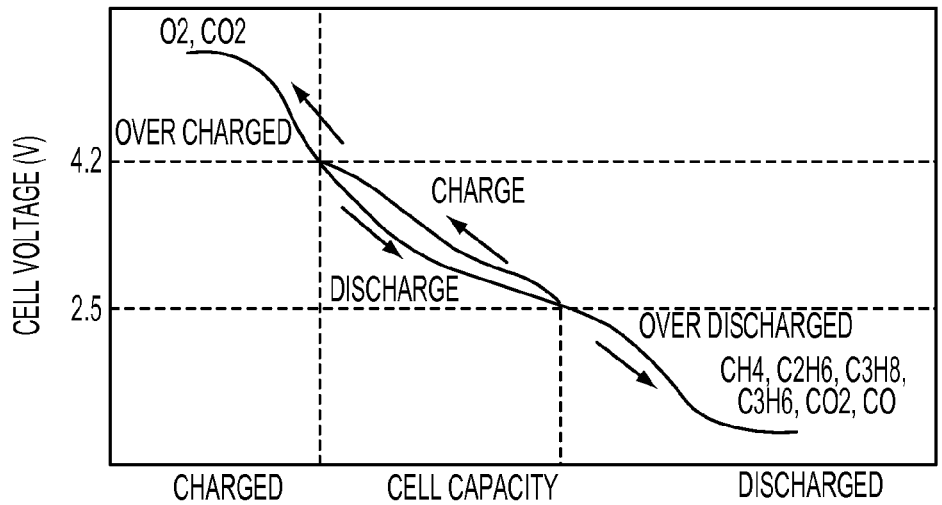
FIG. 1 is a graph that illustrates battery cell operation.

Embodiments disclosed herein involve a battery management approach that is capable of in situ, real-time, chemical gas sensing through optical-based sensors implemented into an energy storage device. Optical sensing of free or dissolved gas in situ during operation of an energy storage device (such as a battery cell) can contribute both to safety and performance of energy storage devices though sensing of multiple parameters. Fiber optic (FO) sensors are made of suitable elements that can withstand various corrosive environments. The thin size of FO cables (typical diameter of 60-500 μm) allows their incorporation as sensor elements into battery cells without significant degradation of battery system performance. In addition, FO sensors in particular can be very useful for chemical sensing to monitor species within the electrochemical energy storage devices with the multitude of complex reversible and irreversible, desirable and undesirable reactions occurring at any point that affect the state of charge, health, and power of the cell.

In terms of performance, the approaches disclosed herein can be useful to cycle an electrochemical cell, e.g., a Li ion or Li polymer battery cell, to its true limits based on the present scenario of environment, age, and use case. With the ability to sense internal cell parameters in real time with embedded fiber optic sensors, it is possible to utilize cells to their true power limits with tighter margins to limits defined by lithium plating and/or other side-reactions associated with overcharge or over-discharge. Improved power performance and charge rate of Li-ion cells is feasible when cells in the pack are driven to their true, safe limits using internal cell sensors to detect precursors to the onset of lithium plating which is typically accompanied by small quantities of gas and chemical evolution that is detectable by embedded fiber optic (FO) sensors.

The ability to monitor gas species or other chemicals inside the cell can also offer an alternative method to measure state of charge (SOC) of a battery to augment or entirely replace electrical cables to externally monitor current and voltage. As one example embodiment of how this might be accomplished, the reversible formation and consumption of gases during ester exchange under nominal operating conditions might be a species of interest to track. Monitoring the gas composition from these reversible reactions with high accuracy can possibly allow for SOC estimation directly. Monitoring pH and/or gases and/or other chemicals reversibly formed or consumed during charge-discharge can be used as SOC indicators.

Considering the safety aspect, cell chemistries create gaseous side-reaction products during adverse conditions, which in addition to overcharge or overdischarge conditions, include abused conditions such as compromised or leaky cells, aged, or otherwise faulty cells. Sensing the products of these side-reactions at early stage in the incipient low concentrations can enable the battery management system to alert the end user about adverse cell behavior.

Furthermore, gas development inside battery cells is a well-known phenomenon towards the end of life (EOL) of a battery cell. An implementation of the proposed sensing scheme is a sensor that gets incorporated into a pouch cell during fabrication of the cell for in situ monitoring chemical parameters, which can be related by an advanced battery management system (BMS) to parameters like State of Charge (SOC), State of Health (SOH) and the (early) prediction of catastrophic failures, thermal runaway, etc.). Optical sensors disposed external to the cell can be used to determine leaks.

For example, if has been demonstrated that $CO_2$ and/or $CH_4$ gas evolution in a Li-ion battery cell significantly increases as the cell approaches overcharged or over-discharged conditions with electrolyte decomposition and other adverse side-reactions. Other chemical species of interest that indicate overcharge or overdischarge include but are not limited to $C_2H_6$, $O_2$, HF, CO, $C_3H_8$, and $H_2$.

Some embodiments described here involve one or more fiber optic sensors inside the cell stack to measure the evolution of gas species in real-time. The optical fiber signal can be analyzed to detect abnormal levels of gas generation. This detection may be based on the fiber optic sensor signal crossing a threshold, or the rate (first time-derivative) of change of the sensor signal (correlated to the rate of gas evolution), or a mathematical combination of both. The battery management unit can then match this sensed abnormality against known markers of adverse reactions inside a cell to regulate or stop battery operation. As a specific example, $CO_2$ evolution can serve as a marker for overcharging, so an abnormality detected from an embedded $CO_2$ sensor signal can be used by battery management unit to stop the charging process.

FIG. 1 is a graph that illustrates battery cell operation. A charge-discharge cycle for the main cell reaction causes the cell to operate within the nominal operating voltage range, e.g., 2.5V to 4.2V in this example. Overcharging the cell causes the cell voltage to rise above this nominal range. Overdischarging the cell causes the cell voltage to fall below this nominal range. While in the overcharged state, the cell may produce excess $O_2$ and/or $CO_2$. While in the overdischarged state, the cell may produce one or more hydrocarbon gases, e.g., $CH_4$, $C_2H_6$, $C_3H_8$, $C_3H_6$ and/or other gases, e.g., $CO_2$, CO.

Figure 2:
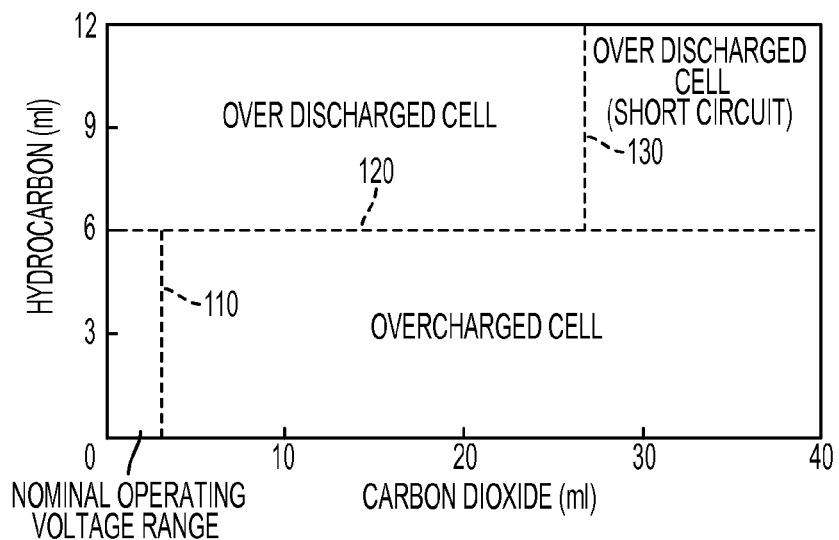
FIG. 2 illustrates the relationship between production of $CO_2$ and hydrocarbon gas for overcharged and overdischarged battery states for a Li-ion battery cell.

FIG. 2 illustrates the relationship between production of $CO_2$ and hydrocarbon gas for overcharged and overdischarged battery states for a Li-ion battery cell. When the battery is operating in the nominal voltage range, there is minimal $CO_2$ gas produced and some hydrocarbon gas produced, e.g., less than 3 ml in this example. As the cell becomes overcharged from the nominal operating range, the amount of $CO_2$ increases and the amount of hydrocarbon gas may also increase. As the cell becomes overdischarged, the amount of $CO_2$ gas may increase and the amount of hydrocarbon gas increases significantly. From this data, detection of $CO_2$ indicates an overcharged cell or a significantly overdischarged cell. Detection of $CO_2$ along with an increase in the amount of hydrocarbon gas over that which is present at the nominal operating range indicates an overdischarge state. Detection of an overcharged cell, an overdischarged cell, and a severely overdischarged cell (short circuit) can be accomplished by comparing amounts of $CO_2$ and hydrocarbon gases detected to threshold amounts that indicate these battery states.

In the illustrated example shown in FIG. 2, if the amount of $CO_2$ is less than threshold 110, e.g., about 3 ml and the amount of hydrocarbon gas is less than threshold 120, e.g., about 6 ml indicate that the cell is operating in the nominal operating voltage range. If the amount of $CO_2$ exceeds threshold 110 and the amount of hydrocarbon gas remains below threshold 120, the cell is determined to be in an overcharged state. If the amount of hydrocarbon gas is greater than threshold 120, the cell is in an overdischarged state. If the amount of $CO_2$ is greater than threshold 130, e.g. about 27 ml in this example, and the amount of hydrocarbon gas is greater than threshold 120, the cell is in an overdischarged, short-circuited state.

Fiber optic sensors embedded within the battery can provide information about internal chemical species concentrations, e.g., free or dissolved gas concentrations in real-time and the information can be relayed to battery management unit within a battery management system. Based on the information relayed from the sensors, the battery management unit may cut-off loads or charge currents at suitably predetermined levels so that off-gas products remain below thresholds for dangerous operation and/or below levels that may lead to accelerated cell aging. In some cases, the approaches described herein can augment or replace monitoring cell terminal voltage to determine if a cell is overcharged or not, which is an indirect and imperfect indicator of overcharge or overdischarge.

Figure 3:
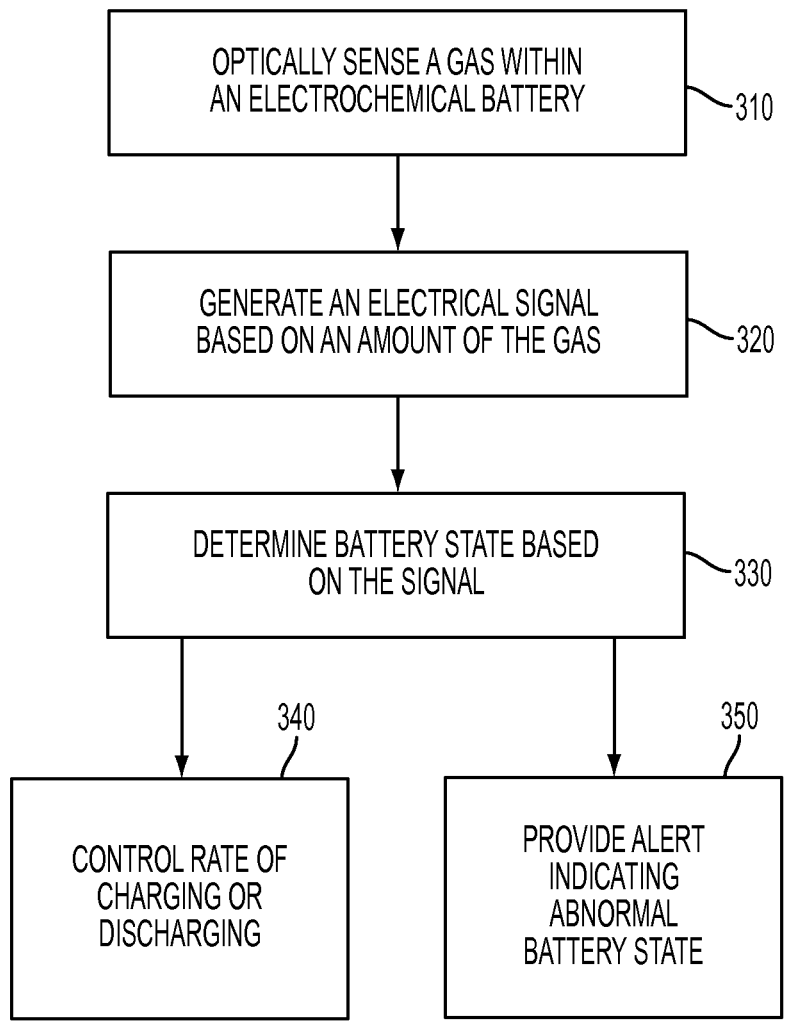
FIG. 3 is a flow diagram illustrating operation of a battery management system according to the approaches described herein.

FIG. 3 is a flow diagram illustrating operation of a battery management system according to the approaches of this disclosure. A free or dissolved gas is optically sensed 310 by optical sensors disposed within the electrochemical battery. Output light from the optical sensor is detected by a photodetector which generates 320 an electrical signal in response to the detected output light. The detector signal includes information from which the battery state can be determined 330. The battery management unit determines the battery state based on the detector signal. For example, the battery management unit may determine that the battery is operating in a normal state and may determine the present state of charge of the battery so that battery charging or discharging can be controlled 340. For example, the battery management unit may be configured to start, stop, and/or adaptively tune the rate at which the battery is charged or discharged. Optionally, the battery management system may include external optical chemical sensors disposed proximate to the battery. Such sensors may be used to detect battery leaks. For example in Li-ion battery cells, hydrocarbon or electrolyte species (such as diethyl carbonate, dimethyl carbonate, and/or ethylene carbonate) detected in the immediate external vicinity of the cell may be an indication of a battery leak. The battery management unit may identify an abnormal state of the battery, such as an overcharged state, an overdischarged state, and/or other abnormal battery states including excessively aged cells, leaky cells, or otherwise compromised or abused cells. In some embodiments, the battery management unit may provide 350 an alert if the information from the optical sensors indicates an abnormal battery state, e.g., overcharged state of the battery, overdischarged state of the battery, leaky cell(s), possible thermal runaway, etc.

FO sensors may be useful for sensors internal and/or external to the cell for chemical and gas detection. External optical sensors may be used for detecting various phenomena of abuse and performance limits being exceeded, which may manifest as seepage of chemicals through the cell skin or seal, such as electrolyte or gas leaks.

Figure 4:
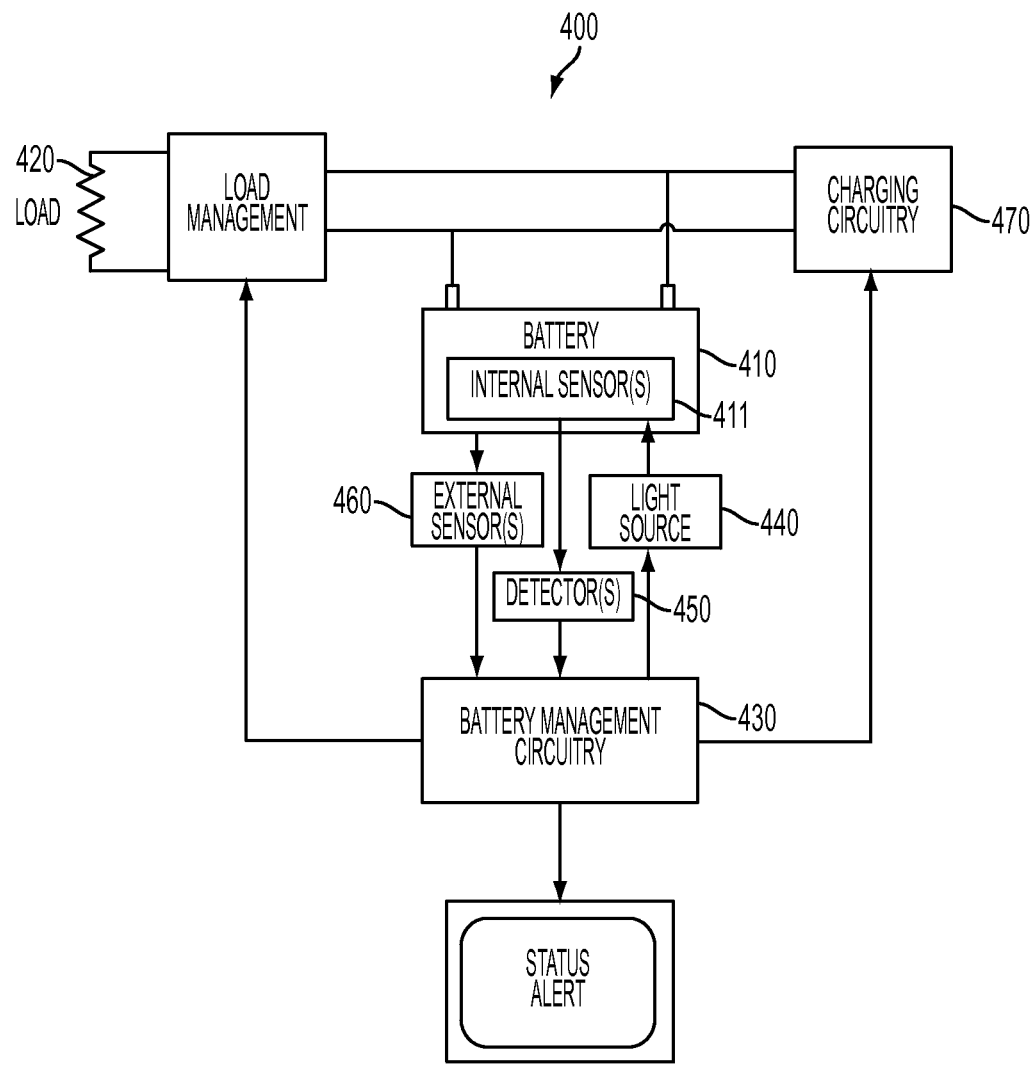
FIG. 4 is a block diagram of a battery management system (BMS) in accordance with some embodiments.

FIG. 4 is a block diagram of a battery management system (BMS) 400 in accordance with some embodiments. The battery management system 400 is shown monitoring a battery 410 that is connected to a load 420. One or more internal sensors 411 are embedded within the battery. At least some of the internal sensors 411 are optical sensors which may measure one or more internal parameters such as temperature, stress, strain, acceleration, ion concentration, chemistry, and/or other internal parameters of the battery 410. At least some of the internal optical sensors 411 are configured to sense free or dissolved gas within the battery.

As discussed in greater detail below, the internal optical sensors may be disposed on an optical fiber or waveguide. Battery management unit 430 is configured to control a light source 440 that provides input light to the internal sensors 411. The light source may comprise, for example, a light emitting diode (LED), laser diode or other type of semiconductor light source In some embodiments, all or part of the battery management unit may be implemented in hardware. In other exemplary embodiments, the battery management unit may be implemented in firmware, software running on a microcontroller or other device, or any combination of hardware, software and firmware.

Each of the optical sensors is optically coupled to an optical detector that is arranged to receive output light from its associated sensor. The detector(s) 450, which are optically coupled to the sensor(s) 411, receive the output light and generate electrical detector signal(s) based on the output light. Thus, each detector signal varies with the amount of the gas sensed by the optical sensor. The detector may be a semiconductor photodiode or other photodetector, for example. The battery management unit 430 receives the detector signal(s) and determines the state of the battery 410 based on the detector signal(s).

In some configurations, the battery management unit 430 may additionally receive signal(s) from external sensor(s) 460 and may use the external sensor signals along with the detector signals to determine the battery state. Using information from both internal sensors and external sensors may provide a more accurate picture of battery state when compared with using external sensors without the use of internal sensors. Furthermore, the implementation of internal sensors as discussed herein may augment or entirely replace the practice of monitoring cell terminal voltage to determine if the cell is overcharged or not. In some embodiments, the external sensors may be optical sensors configured to sense gas leaks and/or seepage of chemicals through the cell skin.

Based on the state of the battery, the battery management unit 430 may control charging circuitry 470 coupled to charge the battery. The battery management unit may control the charging circuitry 470 to stop or start battery charging and/or may adaptively tune the rate of battery charging.

Based on the state of the battery 410, the battery management unit 430 may control discharging of the battery 410. For example, the battery management unit 430 can control load management circuitry 480 to connect or disconnect the load 410 from the battery 410. In some implementations, the load management circuitry 480 can be controlled to vary the load 420 so that the rate of discharging the battery 410 is adaptively tuned.

The battery management unit may optionally be communicatively coupled to a user interface 490 (such as a display) that indicate the battery status to a user visually or aurally, for example. If an abnormal battery state is detected, e.g., overcharge, overdischarge, leaks, etc., the user interface may indicate the abnormal condition to the user.

The battery management unit 430 may implement sensor signal processing and an abnormality detection process using several techniques. Signal processing steps may include pre-processing and feature extraction, followed by detection and diagnosis. Pre-processing is performed to clean the data of noise. Some examples include de-noising, filtering and averaging. Features extracted may be in the time-domain, such as derivatives or statistical moments, in the frequency domain, such as wavelength shift or power spectral density, or in the wavelet domain that combines time- and frequency-domain features.

The detection and diagnosis steps may be data-driven or model-based. Data-driven detection schemes compare the real-time signal to archived data or models built from training data. Such algorithms are usually termed Machine Learning approaches. Some examples include regression, neural networks and support vector machines. In comparison, model-based methods track the sensor data as it evolves over time and compares it to physics-based model predictions. Some examples of model-based approaches include Kalman filtering, particle filtering, and Hidden Markov Models. The detection and diagnosis step may also be implemented by combining data-driven and model-based approaches or any subset of them in a data-fusion framework. For example, end of life of the cell can be predicted using a particle filter or Kalman filter-based approach. Some of the above listed techniques are examples of estimation methods that can learn the underlying trend of degradation and make a probabilistic forecast of end of the life that is continuously updated based on the latest data. Furthermore, if the continuously updated timescale for end of life is suddenly much shorter (e.g., going from a few days/cycles to a few minutes) and and/or the gas concentration signal spikes sharply and suddenly keeps increasing and/or has significant anomalies these are indications of thermal runaway.

During manufacture of a Li-ion battery, the battery layers are assembled and once assembly is complete, the cell undergoes a formation process that involves at least one precisely controlled charge/discharge cycle to activate the materials of the battery and to develop the solid-electrolyte interface (SEI) layer on the anode which allows the battery to function. The controlled charge/discharge of the formation process begins with a low voltage which builds gradually. Using a battery management system comprising internal optical sensors as discussed herein can allow for more precise feedback control over the formation process for the SEI layer.

Typically, Li-ion cells with non-aqueous electrolytes function far outside the thermo-dynamical stability windows of the electrolyte. This leads to electrolyte reduction at the negative electrode, which would make the Li-ion battery a thermodynamically unstable system. Fortunately, for suitable electrolytes the decomposition product of the initial electrolyte-electrode reaction forms a protective film on the anode, the so-called solid-electrolyte surface (SEI). The film acts as a "sieve" which is in first order permeable only to Li+-ions but not to other electrolyte components. The SEI protects both the electrolyte compounds from further reduction and the anode from corrosion. The film formation irreversibly consumes Li-ions, which is why the practical specific capacity of formed cells (i.e. after SEI formation) is typically only 80% to 90% of the originally unformed ones. The formation of the SEI film can be enhanced with regard to its stability and internal resistance by admixture of SEI-stabilizing additives.

The initial SEI formation (during the formation cycles) at the beginning of cycling is connected with electrolyte decomposition and leads both to an impedance rise (gradual contact loss within the composite anode) and gas evolution at the anode. Ongoing SEI formation due to the diffusion of charged/neutral species through the SEI proceeds both during cycling and storing and leads to gas formation and corrosion of $Li_xC_6$ (and hence to further impedance rise, which results in a power fade).

Prior to the SEI formation (or before a sufficiently protective SEI layer is formed), solvent co-intercalation into the graphite leads to exfoliation and cracking of the anode material. In addition to electrolyte reduction inside the graphite, this leads to rapid electrode degradation.

During the SEI layer formation electrolyte is being consumed/decomposed. Consumption of the electrolyte is accompanied with gas formation (e.g., ($CO_2$). Monitoring the CO2 concentration during formation provides a way to monitor the SEI layer formation. During the cell development phase, certain charge and discharge (voltage) cycles are determined which lead to suitable SEI layers. These voltage cycles are then used blind during manufacturing of cells. Active monitoring of SEI layer formation with closed loop feedback information may be used to enhance the development of the SEI layer in comparison with charge and discharged cycles that are used open loop without feedback. During manufacturing it would be possible to react and correct the formation process if slight changes in the environment (e.g. humidity) and/or material composition of electrolyte/electrode material occur. The feedback process for SEI formation may result in more optimal formation cycles, less cracking of the SEI layer, and/or to more homogeneous cells as SEI layer influences the internal resistance of the cell.

Figure 5:
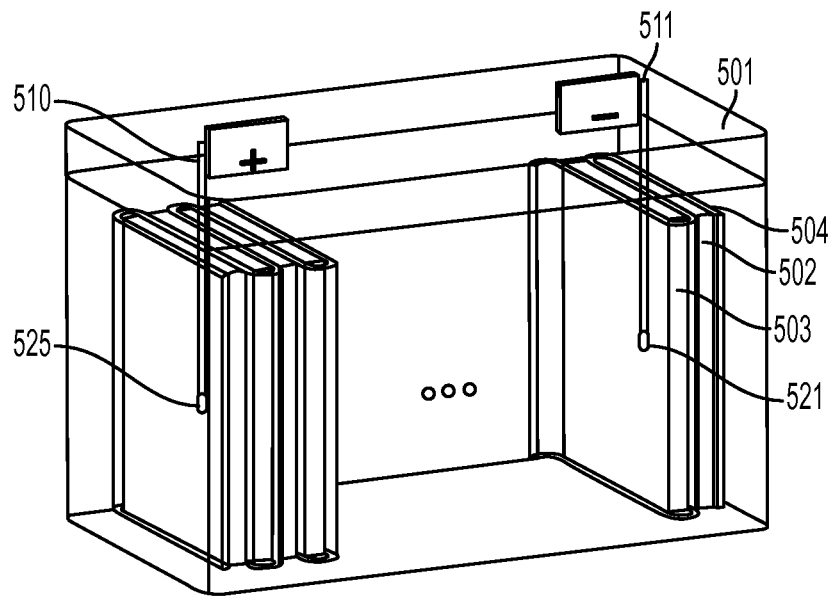
FIG. 5 shows a portion of Li-ion battery having fiber optic cables with fiber optic sensors respectively deployed along the fiber optic cables in accordance with embodiments described herein.

FIG. 5 shows a portion of Li-ion battery 501 having fiber optic (FO) cables 510, 511 having FO sensors 521, 525 respectively deployed along the FO cables 510, 511. The sensors 521, 525 are arranged within the battery 501 at strategic locations. For example, sensor 521 may be configured to sense $CO_2$ and sensor 525 may be configured to sense ph, $CH_4$ or other hydrocarbon gas. The battery includes has an anode 502 and a cathode 503 separated by a spacer layer 504.

Figure 6:
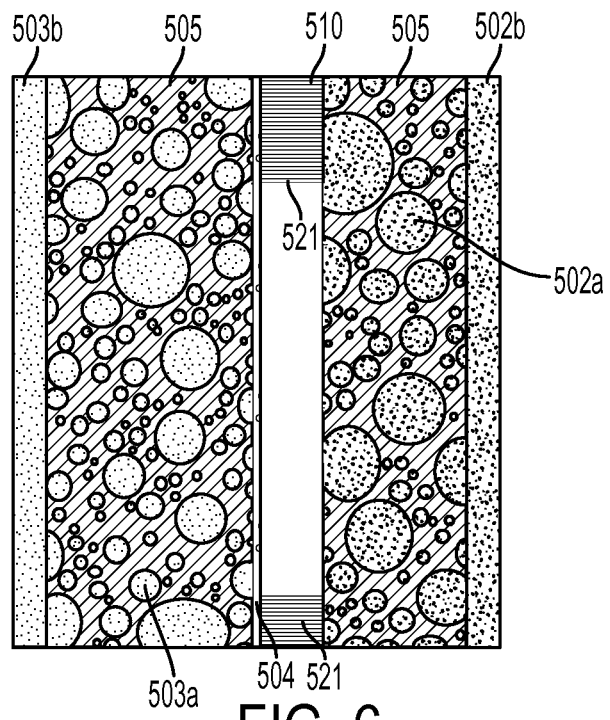
FIG. 6 depicts a zoomed-in cross section of a portion of the battery of FIG. 5 at the location of a sensor.

FIG. 6 depicts a zoomed-in cross section of a portion of the battery 501 at the location of sensor 521. The cathode 503 comprises cathode material 503a disposed within an electrolyte matrix 505 and a cathode collector 503b. The anode comprises an anode material 502a disposed within the electrolyte matrix 505 and an anode collector 502b. The anode 502 and cathode 503 are separated by a separator layer 5504. The portion of the FO cable 510 that includes sensor 521 is embedded within the anode 502, where optical sensor 521 may be used to measure an amount of free or dissolved gas present within the battery.

In some embodiments, the optical sensors comprise a fiber (either single mode or multimode) comprising a FO end tip sensor consisting of a material sensitive to the chemical species to be sensed. The FO sensors are made of suitable elements that can withstand corrosive environments that exist within battery cells. Suitable fiber materials that may be used include fused silica, polymer, etc. The thin size of FO cables (diameter of 60-500 μm) allows their incorporation as sensor elements into battery cells without significant degradation of battery system performance.

Optical sensing can employ optical transduction methods like optical absorption and luminescence to obtain information about the analyte gas. Indirect and/or reagent-mediated FO sensors may be used. In indirect sensing systems, the concentration of an analyte is monitored by the optical characteristics (luminescence, absorption) of an intermediate agent, typically a dye molecule.

To functionalize the fiber for analyte detection, the guided mode field must overlap either directly with the analyte for refractometric or analyte-specific absorption measurements, or with an analyte-specific transducer (e.g., a fluorescent or absorbent dye). This can be achieved in various ways. For example, the fiber cladding can be functionalized, by replacing the cladding with a solid matrix containing the dye or being doped with an indicator (either fluorescent or absorbent). This configuration constitutes an evanescent field sensor. The mode field of the guided modes in the fiber leak out into the analyte sensitive cladding, which changes its optical properties when analyte is present. Sensor configurations with modified cladding are usually interrogated in transmission.

Another example of a useful fiber optic sensor involves reflectance-based measurements. The optical fiber includes a fluorescent coating at the distal end tip of the fiber which is excited by light guided in the fiber. A portion of the occurring fluorescence is coupled back into the fiber, interrogated and processed for either intensity or lifetime measurements.

In some embodiments of reflectance-based sensing, the coating at the tip could be an analyte-specific absorption layer. The input light is reflected from the tip and the reflected light is measured by a detector to determine differences between the input light and the reflected output light. In some implementations, an optional mirror positioned after the sensing layer could be added to increase reflection.

In absorption-based sensing, colorimetric $CO_2$ detection can be achieved by measuring the change in pH value of an indicator in reaction to the formation of carbonic acid ($H_2CO_3$) due to the contact with acidic $CO_2$ gas.

$$CO_2(g) \overset{K_1}{\rightleftharpoons} CO_2(aq) \quad (1.1)$$

where $K_1 = 3.4 \times 10^{-2}$ mol dm$^{-3}$ atm$^{-1}$ $$CO_2(aq) + H_2O \overset{K_2}{\rightleftharpoons} H_2CO_3 \quad (1.2)$$

where $K_2 = 2.6 \times 10^{-2}$ $$H_2CO_3 \overset{K_3}{\rightleftharpoons} H^+ + HCO_3^- \quad (1.3)$$

where $K_3 = 1.72 \times 10^{-1}$ mol dm$^{-3}$ $$HCO_3^- \overset{K_4}{\rightleftharpoons} H^+ + CO_3^{2-} \quad (1.4)$$

where $K_4 = 5.50 \times 10^{-11}$ mol dm$^{-3}$

The fundamental reaction principle imposes some requirements on the host matrix besides the ability to prevent the analyte from leaching while keeping it accessible to the analyte. As can be seen from Equ. 1.2, the host matrix retains water which is used in the formation of carbonic acid. Furthermore, the host matrix allows for ingress of protons formed during reactions 1.3 and 1.4 in order to enable the indicator to the change its optical properties with varying pH value. For fiber based optical sensors, host matrix is applied in form of a fiber cladding or tip coating.

Polymer matrices can be used as host matrices for optical reagent mediated sensors. In comparison to sol-gel matrices, they are better suited for high temperature applications. Frequently used materials include polystyrene (PS), polyvinyl chloride (PVC), polymethyl methacrylate (PMMA), polydimethyl siloxanes (PDMS), polytetrauoroethylenes (PTFE) and cellulose derivatives like ethyl cellulose. Especially the latter one is, due to its more hydrophilic nature, better suited for pH (and therefore $CO_2$) measurements than for example PMMA and PDMS, which are both hydrophobic.

Sol-gel matrices are basically porous glass matrices into which the reagent is encapsulated in a cage-like structure and into which the analyte can diffuse. The term "sol-gel" stands for the actual process of producing solid materials from small molecules. A monomer gets converted into a colloidal solution (sol) which acts as a precursor for an integrated network (gel) of discrete particles or network polymers. Process parameters like precursor type and concentration, water content and curing temperature can be used to enhance the matrix structure and hence the sensor performance.

For absorption based sensing of $CO_2$, the same indicator dyes are used as for colorimetric pH sensing. The most common ones are thymol blue (immobilized in a sol-gel matrix) and bromothymol blue (in an ionic liquid matrix). The skeletal structures for both indicators are shown below.

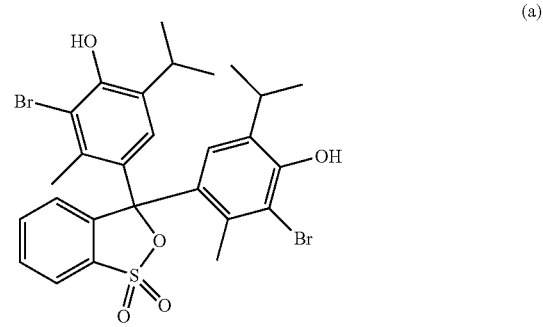

(a)

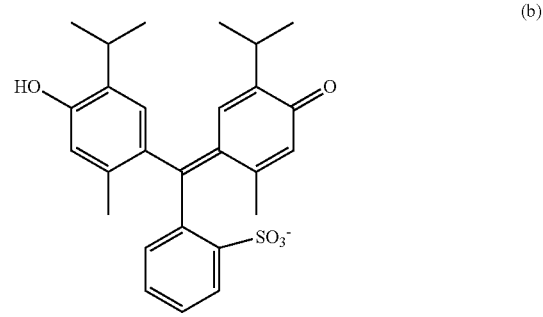

(b)

Luminescent based sensing for $CO_2$, and in general for many other analytes like pH, ammonia, $O_2$, etc., is intrinsically more sensitive than absorption-based sensing methods. As is the case for absorption-based sensing of $CO_2$, luminescence measurements for carbon dioxide are based on the detection of a change of the pH value by an indicator dye. For the chemistry to be detected, again two fluorescent probes are popular, fluorescein and 8-hydroxypyrene-1,3,6-trisulfonic acid (HPTS). Recently, luminescent transition metal complexes showed larger Stokes shifts and longer lifetimes compared to fluorescein and HPTS. This allows for more robust read out concepts like emission life time measurements, which are not prone to intensity-based fluctuations due to light source instabilities, etc. For example, some Ruthenium(II) complexes like Ru(dpp)3 show very long unquenched lifetimes, up to ~5 μs. Once paired with pH sensitive indicators for optical $CO_2$ detection, the dye gives rise to a non-radiate energy transfer with increasing H+ concentration which in turn decreases the luminescence lifetime of the Ruthenium(II) complex. Although the above paragraphs describe $CO_2$ sensing, it will be appreciated that similar concepts can be applied to sensing of $O_2$ and/or other gases.

There are several approaches for reading information from the optical sensors including intensity-based techniques and techniques based on lifetime phase measurements. The process of obtaining the fluorescence lifetime employing phase measurements is referred to as the frequency domain method (FDM). The sensor is illuminated by an excitation source which is modulated with a frequency f. Hence the fluorescent emission is also modulated with exactly the same frequency, but experiences a phase shift that happens to be dependent on the fluorescence lifetime:

$$\tan(\Phi) = 2\pi f \tau \quad (2)$$

where $\Phi$ is the phase angle, f is the modulation frequency of the light and $\tau$ is the fluorescence lifetime. By measuring the phase angle between the excitation and the emission signal, the emission lifetime of the fluorescent dye can be calculated. Low-cost light sources such as light emitting diodes (LEDs) can be used to provide input light for excitation, and in combination with inexpensive photodiode detectors and a sufficiently long-lived indicator complex, a relatively inexpensive optoelectronic read out system can be designed.

To overcome the need for long-lived fluorescence dyes in lifetime measurements, multiple principles have been developed to enable rendering intensity-related information into the frequency domain, where the intensity-related information is accessible via phase measurements.

In the following pages, techniques are described which enable rendering intensity-related information into the wavelength domain. The described read-out enables interrogation of the intensity-encoded analyte information as a spectral shift (centroid shift) in the output light. These techniques represent one particular example for obtaining information from intensity-encoded sensors which may be disposed internally within a battery, e.g., the colorimetric sensing layers described above. The described techniques illustrate a few examples of intensity-based optical sensing and it will be understood to those skilled in the art that many other techniques for obtaining intensity-coded information from optical sensors are also possible and are considered to fall within the scope of this disclosure.

Figure 7:
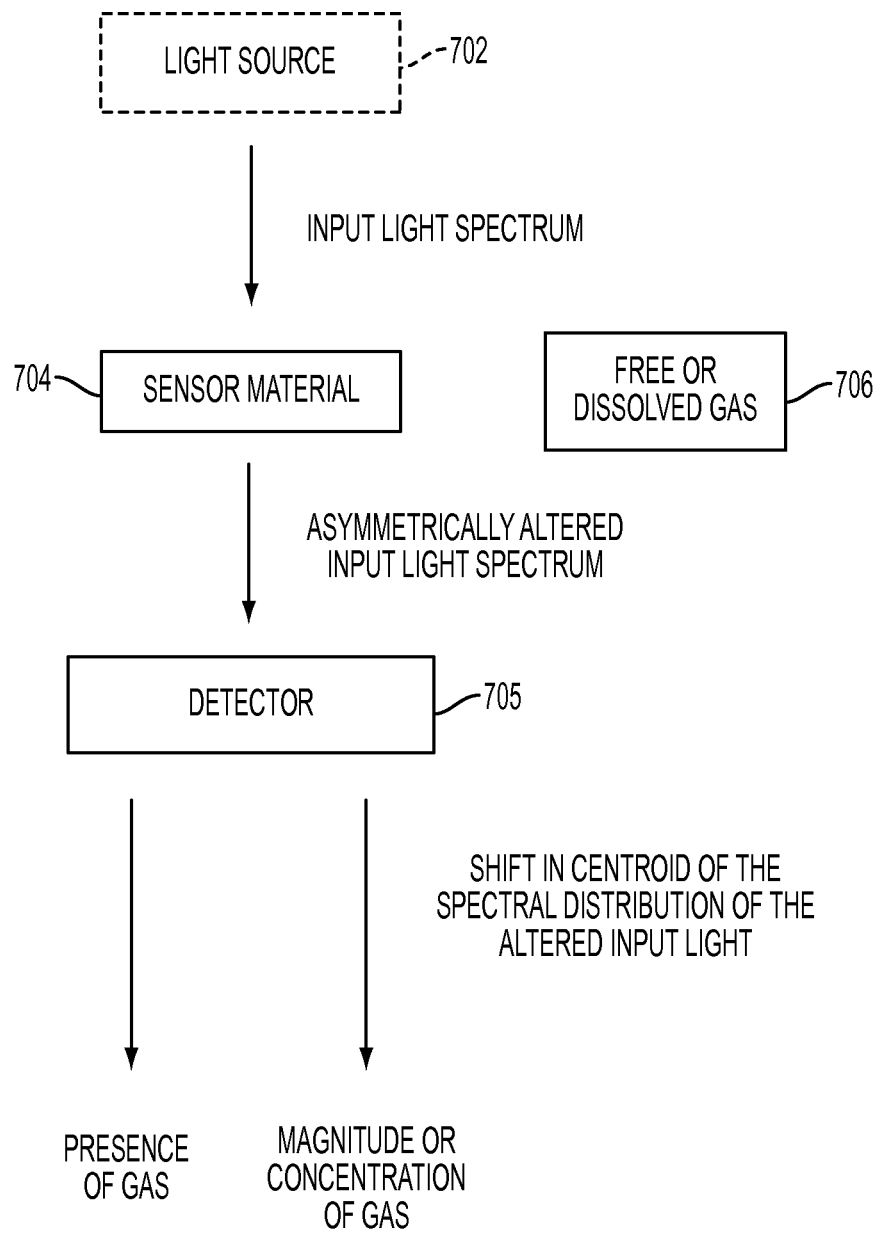
FIG. 7 is a block diagram of a system for detecting presence of a gas within a battery cell using an optical-based detector in accordance with various embodiments.

FIG. 7 is a block diagram of a system for detecting presence a gas within a battery cell using an optical-based detector in accordance with various embodiments. The system shown in FIG. 7 includes sensor material 704 arranged to interact with input light generated by a light source 702. The sensor material 704 is designed to asymmetrically alter a spectral distribution of the input light in response to presence of the gas 706. The system shown in FIG. 7 further includes a detector 708 configured to sense the altered input light and to generate at least one electrical signal comprising information about a location of a centroid of a spectral distribution of the altered input light. The detector 708 is configured to directly measure a shift in the centroid of the altered input light relative to a centroid of the spectral distribution of the input light rather than determining the spectral distribution itself. The detector 508 may further be configured to determine the magnitude or concentration of the external stimulus sensed by the sensor material 704.

According to some embodiments, the sensor material 704 comprises analyte-specific sensor material. In the presence of a specific analyte, an optical property of the analyte-specific sensor material 704 changes in a specified spectral range of the input light spectrum. Representative optical properties of the analyte-specific sensor material 704 that can change in the presence of a specified analyte include absorption, transmission, scattering, light emission or reflection in the specified spectral range. A change of the optical property of the analyte-specific sensor material due to presence of the specific analyte asymmetrically alters the spectral distribution of the input light. The detector 705 is configured to determine a shift in the centroid of the altered input light relative to a centroid of the spectral distribution of the input light in response to presence of the specific analyte sensed by the sensor material 704. The detector 705 can also determine the magnitude or concentration of the analyte sensed by the sensor material 704. For example, the shift of the centroid of the spectral distribution of the input light is related to the change in analyte concentration or the change in magnitude of another form of external stimulus. After calibration and/or referencing, such as to a detector without a sensing layer, the detector 705 can directly measure the analyte concentration or stimulus amplitude.

According to some embodiments, the sensor material 704 is arranged to interact with input light and asymmetrically alters a spectral distribution of the input light in response to presence of a specific gas concentration or gas concentration range. In such embodiments, the sensor material 704 can include Binuclear Rhodium Complexes for CO detection or Bromocresol purple for $NH_3$ detection, and the specific gas concentration can be defined in the 50-80000 ppm (0.005%-8% partial pressure) range for CO and 5-1000 ppm for $NH_3$, for example.

Figure 8:
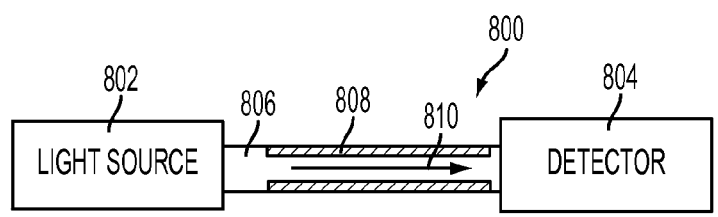
FIG. 8 illustrates a portion of a battery management system configured for detecting presence of a free or dissolved gas within a battery using an optical-based sensor interrogated in transmission mode in accordance with various embodiments.

FIG. 8 illustrates a portion of a battery management system configured for detecting presence of a free or dissolved gas within a battery using an optical-based sensor 800 interrogated in transmission mode in accordance with various embodiments. In the embodiment shown in FIG. 8, the system includes a light source 802 and a detector 804 spaced away from the light source 802. The light source 802 and the detector 804 are disposed external to the battery. The light source 802 can include a light emitting device, such as a light emitting diode (LED), a laser diode or a semiconductor laser, for example. An optical wave guide (e.g. optical fiber) 806 is disposed between the light source 802 and the detector 804 and may be disposed within the battery (not shown in FIG. 8). In some cases, one or more optical connectors (not shown in FIG. 8) may be arranged externally to the battery and/or on the battery case to optically couple the optical fiber 806 to the light source 802 and detector 804. Sensor material 808 is situated in the optical wave guide 806 to interact with the guided light 810. In the case of an optical fiber, the whole or a part of the cladding material can be replaced by the analyte/stimulus specific sensing material.

Figure 9:
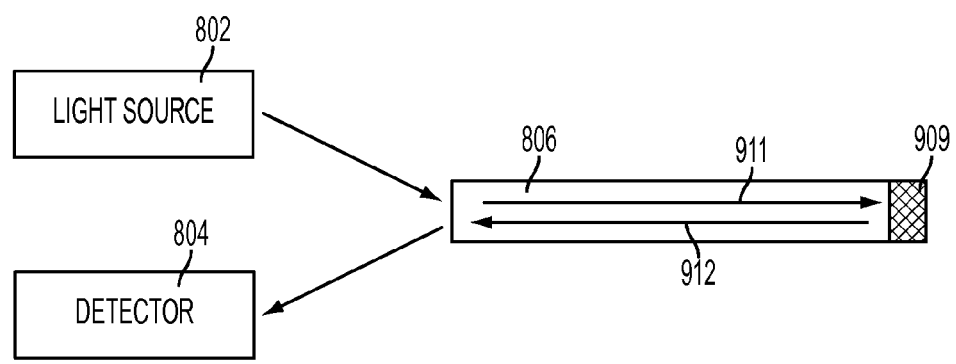
FIG. 9 illustrates a portion of a battery management system configured for detecting presence of a free or dissolved gas within a battery using an fiber optic end tip sensor interrogated in reflection mode in accordance with various embodiments.

FIG. 9 illustrates a portion of a battery management system configured for detecting presence of a free or dissolved gas within a battery using an fiber optic end tip sensor 909 interrogated in reflection mode in accordance with various embodiments. In the embodiment shown in FIG. 9, the system includes a light source 802 optically coupled to the optical fiber 806 and configured to provide input light 911 to the optical fiber. A detector 804 is optically coupled to the optical fiber 806 and is configured to receive reflected light 912 that is reflected from the end of the optical fiber 806. The light source 802 and the detector 804 are disposed external to the battery. At least the end portion of the optical fiber is disposed within the battery. Sensor layer 909 is situated at the end tip of the optical fiber 806 and is sensitive to the gas of interest. The sensor material 909 interacts with the input light 911 such that reflected light 912 is different from the input light 911.

In general, the light source 802 should be a broad band light source so that the sensing layer 808, 909 can asymmetrically alter the spectrum. Laser sources emitting a plurality of laser modes can also be used. In the case of inelastic scattering (Raman scattering), the spectral range impacted by the sensing layer 808, 909 can be quite narrow and, therefore, so can that of the spectral distribution of the light source (e.g., laser). As a general rule for a sensitive system, the spectral distribution of the input light should be about twice as broad as the affected spectral range of the sensing layer 808, 909. In this case, the sensing layer 808, 909 can most effectively asymmetrically modify the spectral distribution of the input light.

The light source 802 can include a light emitting device, such as a light emitting diode (LED), a laser diode or a semiconductor laser, for example. An optical wave guide (e.g. optical fiber) 806 is disposed between the light source 802 and the detector 804 and may be disposed within the battery (not shown in FIG. 8). In some implementations, one or more optical connectors (not shown in FIG. 8) may be arranged externally to the battery and/or on the battery case to optically couple the optical fiber 806 to the light source 802 and detector 804.

As illustrated by FIGS. 8 and 9, the battery management system can include an LED as a light source 802 coupled into an optical fiber 806 which is coated with a gas-specific coating 808, 909 disposed along the length of the optical fiber or disposed at the end time of the optical fiber. The sensing layer 808, 909 has one or more optical properties that change in the presence of a specific gas. The input light produced by the LED is preferably broad band light with a certain center wavelength and FWHM (Full-Width Half-Maximum). The presence of the gas changes the transmission properties of the gas-specific coating 808, 909 on the fiber 806 in a certain spectral range. Depending on the nature of the sensing layer 808, 909 the presence of the gas can either increase or decrease the absorption in this spectral range according to some embodiments.

The sensing layer spectrum and LED spectrum can be chosen so that the presence of an gas causes a change in the spectral distribution (e.g., centroid of the spectral distribution) of the LED spectrum. In some embodiments, the detector comprises a wavelength centroid detector 804 that is configured to measure a wavelength shift of the centroid of the spectral distribution of the altered input light (the gas-induced changes of the LED spectrum) and to measure the gas concentration.

According to various embodiments, the presence of a gas causes a change in the sensing layer 808, 909. A change in the sensing layer 808, 909, causes a change in light that interacts with the sensing layer 808, 909 in a certain spectral range. The interacting light may be transmitted, scattered, emitted (fluorescence) or reflected. A change in the sensing layer 808, 909 caused by the gas (also referred to herein as the analyte) alters the spectral distribution of the input light such that output light (light that has interacted with the sensing layer 808, 909) has a different spectral distribution from the input light emitted from light source 802. The gas concentration can be deduced from changes of a centroid of the spectral distribution (e.g., color change) of the altered input light (the output light). The center wavelength of the input light (e.g., filtered white light, LED or RC LED, broad band or multiple wavelength emission laser) and the center wavelength of the analyte-induced intensity change should not be centered. In some embodiments, a greater change in the centroid of the input light can be achieved if the analyte affects only one half of the incoming light spectrum. According to such embodiments, the sensing layer 808, 909 is arranged to asymmetrically alter a spectral distribution of the input light in response to presence of a specific gas, such that only one half of input light spectrum is affected by presence of the gas.

Provided herein are several representative implementations of fiber based systems, such as systems with a coated LED or LED array. It is understood that the principles disclosed herein can be employed in many other analogous or similar implementations. Many of the representative examples provided herein use sensing layers which modify the centroid of the incoming light spectrum by creating absorption dips in the transmitted or reflected spectrum. It is understood that a sensing layer that provides for analyte-induced changes in other optical properties (elastic or inelastic light scattering, reflection, fluorescence emission, etc.) can be used to modify the spectral distribution of the incoming light. Embodiments of the disclosure provide for measuring a shift of the wavelength distribution of altered input light rather than determining the intensity at a certain wavelength (band), which is elegant and relatively simple since it does not require any wavelength referencing, thus enabling the implementation of very low cost systems.

The readout of intensity-encoded sensors, both fiber-based sensors and non-fiber-based sensors, is typically accomplished by intensity measurements, either via analyzing the optical spectrum at a certain wavelength or by illumination with a light source of certain spectral range (which spectrally overlaps with the absorption spectrum of sensing layer) and measurement of the intensity of the light after interaction with the sensing later is recorded. In order to increase sensitivity, often a second wavelength which does not spectrally overlap with the absorption spectrum is measured for reference. Examples for absorption-based fiber sensors are evanescent wave absorption-based fiber sensors. The evanescent field of the guided light in the fiber overlaps with the sensing agent directly or with a transducing material (e.g., coating, in cladding incorporated dye, etc., in general called "sensing material" in the following discussion). The propagation of the evanescent light wave through this region is connected with higher losses compared to the fiber core. Furthermore, the losses sensed by the evanescent field alter with the concentration of agent to be sensed. Hence, the intensity of the transmitted light through the fiber depends on the agent concentration.

According to various embodiments, the detection methodology disclosed herein exploits the fact that the centroid of the absorption spectrum of the sensing layer is different when compared to the centroid of the input light source. In other words, the absorption spectrum of the sensing layer is placed non-centered in the illumination spectrum of the light source and thus sees a monotonic baseline.

Figure 10:
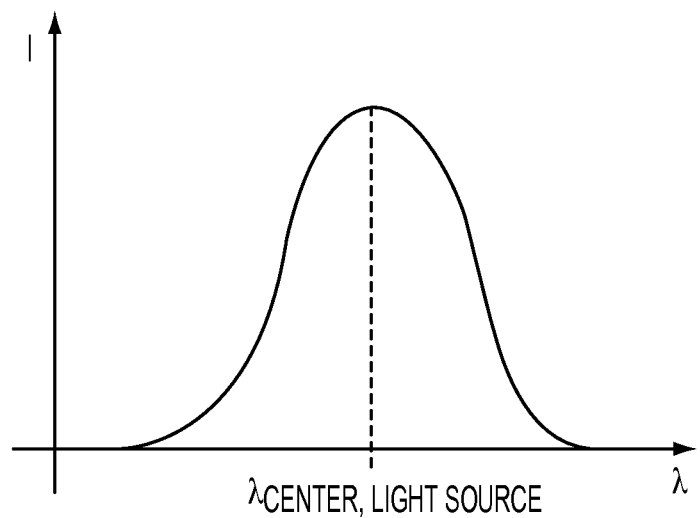
FIG. 10 shows the spectrum of a representative illuminating light source that can be used in a battery management system in accordance with various embodiments.
Figure 11:
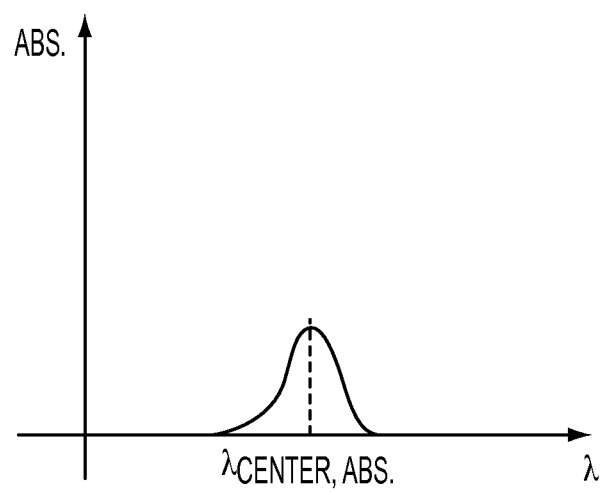
FIG. 11 shows the absorption spectrum of a sensing layer that can be used in a fiber optic sensor disposed within a battery and configured to sense for free or dissolved gas present within the battery in accordance with various embodiments.
Figure 12:
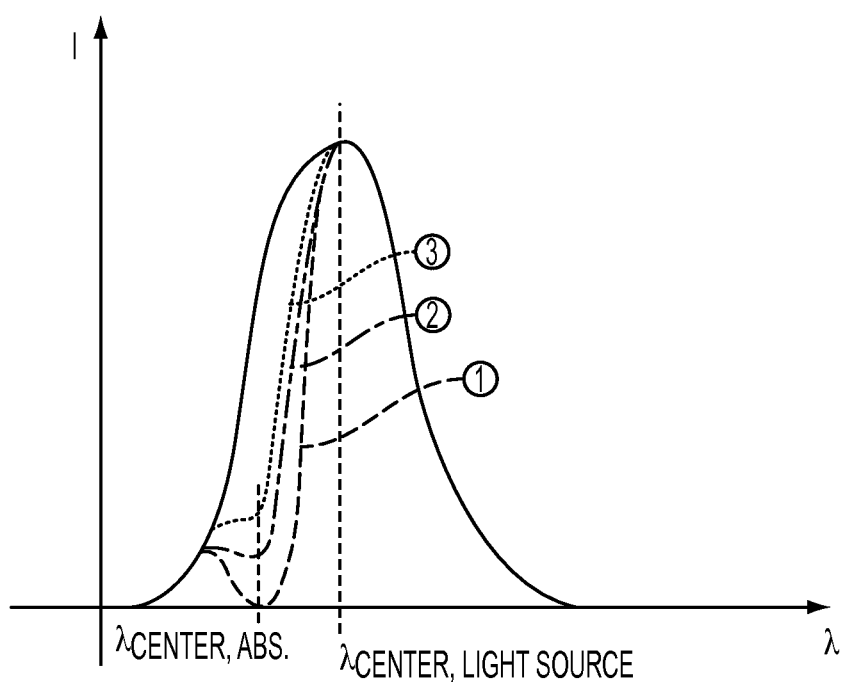
FIG. 12 shows a representative light source spectrum as shown in FIG. 10 affected by a representative absorption spectrum of a sensing layer as shown in FIG. 11.

By way of example, FIG. 10 shows the spectrum of a representative illuminating light source. The illuminating light source of FIG. 10 may be a (spectrally filtered) tungsten-halogen bulb, an LED, an RC LED or a laser emitting multiple wavelengths, for example. It is understood that the spectrum shown in FIG. 10 is provided for illustrative purposes, and can look considerably different for different light sources. The representative light source spectrum shown in FIG. 10 has a center wavelength given by $\lambda_{center,Lightsource}$. FIG. 11 shows the absorption spectrum of a sensing layer, such as the sensor material shown in FIGS. 8 and 9. The representative absorption spectrum shown in FIG. 11 has a center wavelength given by $\lambda_{center,Abs}$. FIG. 12 shows a representative light source spectrum affected by a representative absorption spectrum of a sensing layer. The center wavelengths of the two spectra are labeled $\lambda_{center,Lightsource}$ and $\lambda_{center,Abs}$, respectively. For good performance, the illumination spectrum of the light source should be chosen broader than the absorption spectrum, so that the absorption spectrum can be positioned non-centered within the illumination spectrum, as is shown in FIG. 12. Hence, the centroid of the input light spectrum is different from the centroid of the illumination spectrum after interacting with the sensing layer. In FIG. 12, three different absorption levels of the sensing layer are shown respectively as broken lines 1, 2, and 3.

In accordance with various embodiments, it is important for the functionality of the detection method that the absorption spectrum of the sensing layer is placed non-centered within the illumination spectrum of the input light source. In some embodiments, the absorption spectrum can be predominantly incorporated into 'one half' of the illumination spectrum (e.g., the left side or right side relative to the center wavelength). In the illustrative embodiment of FIG. 12, it can be seen that the absorption spectrum of the sensing layer is predominantly incorporated into the left half of the illumination spectrum of the light source.

It is noted that the steeper the illumination spectrum is relative to the width of the absorption spectrum, the more sensitive the detection scheme will be with respect to changes in the absorption characteristics. However, in general, the sensing layer should only change the centroid of the illuminating light source with different analyte concentrations. Thus, the absorption spectrum could also be implemented such that it affects both sides of the illumination spectrum, as long as the centroid of the illuminating light source is altered by the sensing layer, rather than being incorporated into one side of the illumination spectrum. It is further noted that the FWHM of the absorption band can also be as broad as or even broader than the FWHM of the illumination light. In this case, the two bands should be off-centered far enough so that the absorption spectrum effectively eats away one half of the illumination spectrum. However, this configuration is less preferred since it lowers the sensitivity of the sensing system. In this case, only a portion of the absorption band of the sensing layer overlaps with the incoming light and alters its spectral distribution.

In some embodiments, rather than using a broad band illumination source, a laser emitting multiple emission wavelengths (e.g., special multi wavelengths (or broad band laser) diode) or a combination of laser diodes can be used. In such embodiments, a portion of the emission wavelengths are affected by the absorption band of the sensing layer, while another portion is not affected. This relative change in the intensity of the emission wavelengths can be measured with one wavelength centroid detector measuring the spectral shift of the centroid of the emission lines.

As previously discussed, the interaction of the light source with the sensing layer should be determined using a wavelength centroid detector which measures the centroid of the spectral input light distribution. There are many interrogation approaches that can be used for this purpose. Particularly suited for this purpose is a wavelength shift detection methodology that effectively converts the task of measuring the wavelength of the incoming light to measuring precisely the position of a light spot on a position-sensitive detector. The wavelength information is encoded into position information via a detector comprising a lateral varying coating. One useful detector, for example, is a compact and fast wavelength monitor that can resolve sub-pm wavelength changes.

Figure 13:
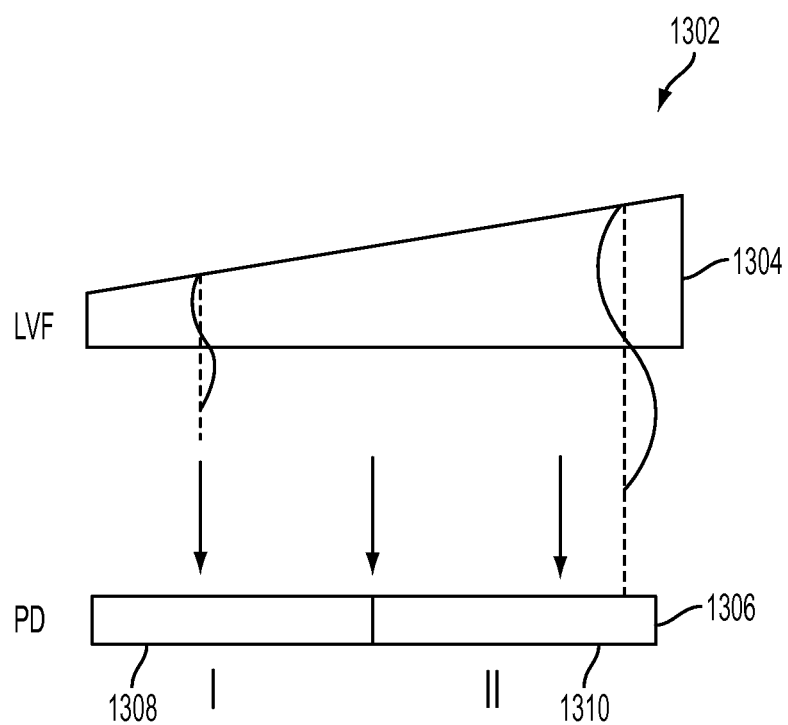
FIG. 13 illustrates a detector that can be used to detect free or dissolved gas in conjunction with a battery management system in accordance with various embodiments.

According to some embodiments, and with reference to FIG. 13, there is shown a detector 1302 that includes a position sensing device 1306 and a filter 1304 (e.g., linear variable filter) that cooperate to convert the wavelength information of the incident light into a spatial intensity distribution on the position sensing device 1306. Differential read-out of two adjacent elements 1308 and 1310 of the position sensing device 1306 is used to determine the centroid of this distribution. A wavelength change of the incident light is detected as a shift of the centroid of the distribution. The detector 1302 serves as a wavelength monitor, which can be used as a readout unit for any optical sensor that produces a wavelength shift in response to a stimulus.

With further reference to FIG. 13, the wavelength information of the altered input light is converted via the filter 1304 into spatial information. Different filter approaches can be used, for example bandpass filters with slightly different characteristics or a linear variable filter as previously discussed. A linear variable filter 1304 transmits light of a certain wavelength only at a certain position, and therefore acts as a position-dependent bandpass filter. As an example, for the linear variable filter 1304 shown in FIG. 13, shorter wavelengths get transmitted on the left side, while longer wavelengths get transmitted at the right side. The transmitted light is detected by the position sensing device 1306, such as a photodiode (PD), which can be split in the middle according to some embodiments, a so-called split diode. The two separated regions 1308 and 1310 of the split diode of position sensing device 1306 can be called region I and region II, which are also shown in FIG. 13. One half of the wavelength spectrum transmitted through the filter 1304 is detected by region I of the position sensing device 1306, whereas the other half of the wavelength spectrum is detected by region II of the position sensing device 1306.

Thus, from the resulting photocurrents of the photo detector regions 1308 and 1310 (which is proportional to the absorbed photons), the centroid of the light distribution in the wavelength regime can be determined, such as by taking the difference of the photocurrents from detection region I and II and dividing this difference by the sum of the photocurrents.

By comparing the photocurrent produced by the adjacent detector elements 1308, 1310, a measure for the actual position of the centroid of the transmitted light is obtained. In order to make the read-out signal stable against intensity fluctuations, the signal can be normalized by the total incoming intensity and is typically called Differential Signal (S_Diff), which can be expressed as:

$$\text{Centroid of Light Distribution} \sim S\_Diff = \frac{I_1 - I_2}{I_1 + I_2}$$

Figure 14:
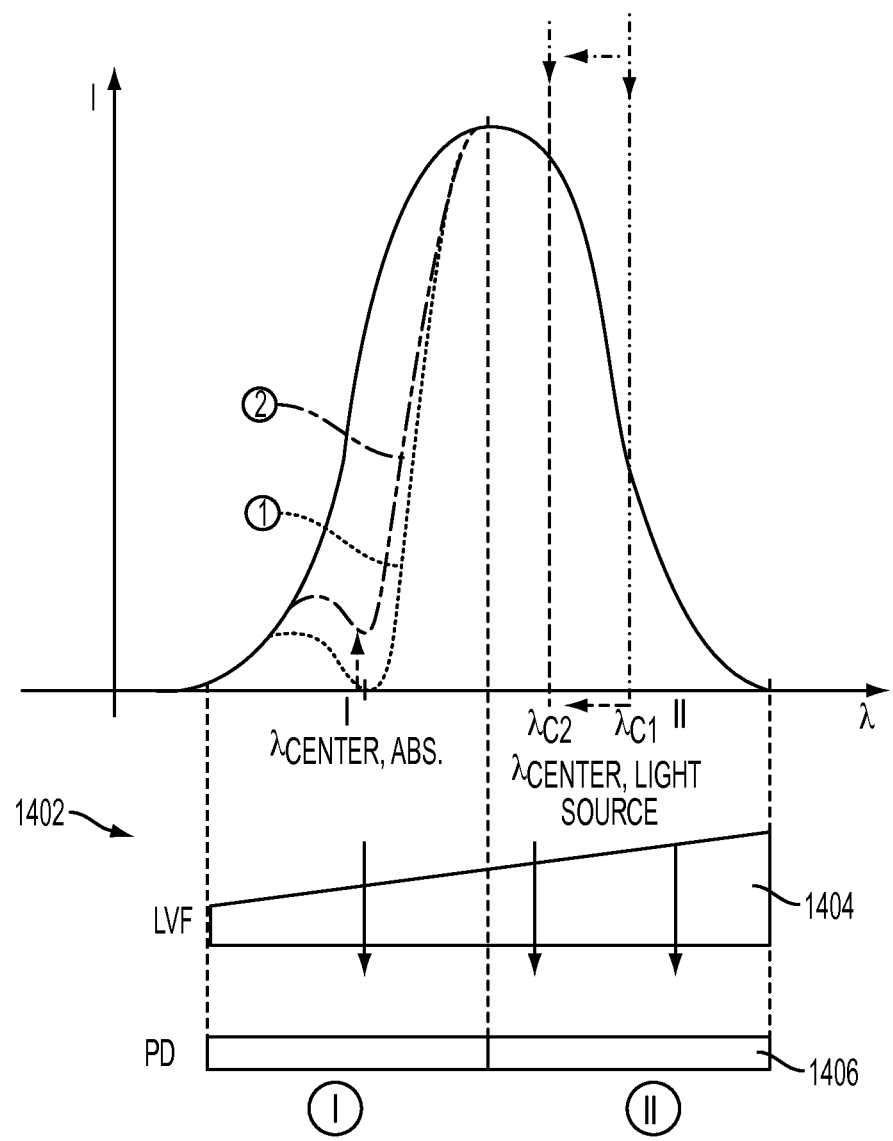
FIG. 14 shows a detector for a battery management system in accordance with various embodiments.

FIG. 14 shows a detector for a battery management system in accordance with various embodiments. In the embodiment illustrated in FIG. 14, the sensing layer optical sensor has an absorption spectrum which is incorporated completely into one half of the illuminating spectrum of the light source to provide for increased sensitivity. The detector 1402 includes a wavelength-dependent filter 1404 (e.g., a linear variable filter or LVF) which is designed so that its full spectral range just incorporates the illumination spectrum. Hence, the center wavelength of the filter 1404 is the same as the center wavelength of the light source. A position sensing device 1406, according to some embodiments, includes a photodiode (PD), which can be implemented as a split photodiode (regions I and II) centered to the filter 1404. Two representative cases are highlighted in FIG. 14 (see curves 1 and 2) for purposes of illustration. It is noted that, depending on the transducing mechanism, the light source spectrum does not necessarily have to be changed in the described manner. For example, the absorption can increase with analyte concentration instead of decreasing behavior here or fluorescence can occur, for example.

In the context of FIG. 14, the light source spectrum is altered by the absorption characteristics of the sensing layer, which may also be referred to a transducing material. The illuminating light source can be characterized by a certain FWHM and a center wavelength $\lambda_{center,Lightsource}$. The absorption characteristic of the sensing layer can be described by a certain FWHM and a center wavelength $\lambda_{center,Abs}$. As previously discussed, the filter 1404 can be a linear variable filter (LVF) and the photodiode (PD) of the position sensing device 1406 can be a split-diode with photodiode sections I and II. The detection ranges for the two photodiode sections I and II are also marked in the spectrum plot on the wavelength axis (x axis), as indicated by the dashed lines extending from the position sensing device 1406 to the wavelength axis. Two different situations with different analyte concentrations are shown in spectra 1 and 2 shown in FIG. 14. In situation 1, no analyte is present; hence the absorption dip is largest and the centroid of the light source spectrum lies on the right side (labeled as $\lambda_{C1}$). If the analyte concentration increases, the absorption dip decreases, as is indicated by spectrum 2. Hence, the centroid of the light distribution on the position sensing device 1406 shifts to the left, as is indicated by a different centroid wavelength $\lambda_{C2}$, in this case. This shift of the centroid leads to a change in the photocurrent in regions I and II, and therefore changes the position sensing device output signal S_Diff, as described above. It is noted that the shift in centroid of the wavelength is exaggerated in FIG. 14 for better visualization. In a real application, the shift might be smaller. However the position sensing device 1406 described above is highly sensitive even to the slightest changes of the centroid.

EXAMPLE 1

No Analyte Present

When no analyte is present, maximal absorption around the absorption center wavelength $\lambda_{center,Abs}$ occurs. The position sensing device 1406 determines the centroid of the spectral distribution by comparing the intensities on both photodiode sections I and II to each other. As significant absorption takes place in the left side of the spectrum (photodiode I), more photons get transmitted in section II (and therefore larger photocurrent gets produced in section II) and hence the centroid of the altered light source spectrum lies somewhere right of the light source center wavelength $\lambda_{center,Lightsource}$ and can be called $\lambda_{C1}$.

EXAMPLE 2

Analyte Present

When an analyte specific to the sensing layer is present, absorption of the sensing layer is decreased and the absorption dip decreases slightly. In comparison to Example 1 above, more photons now get transmitted onto photodiode I and the centroid of the altered light source spectrum $\lambda_{C2}$ shifts to the left, yet still remains in the right section of the light source spectrum.

Figure 15:
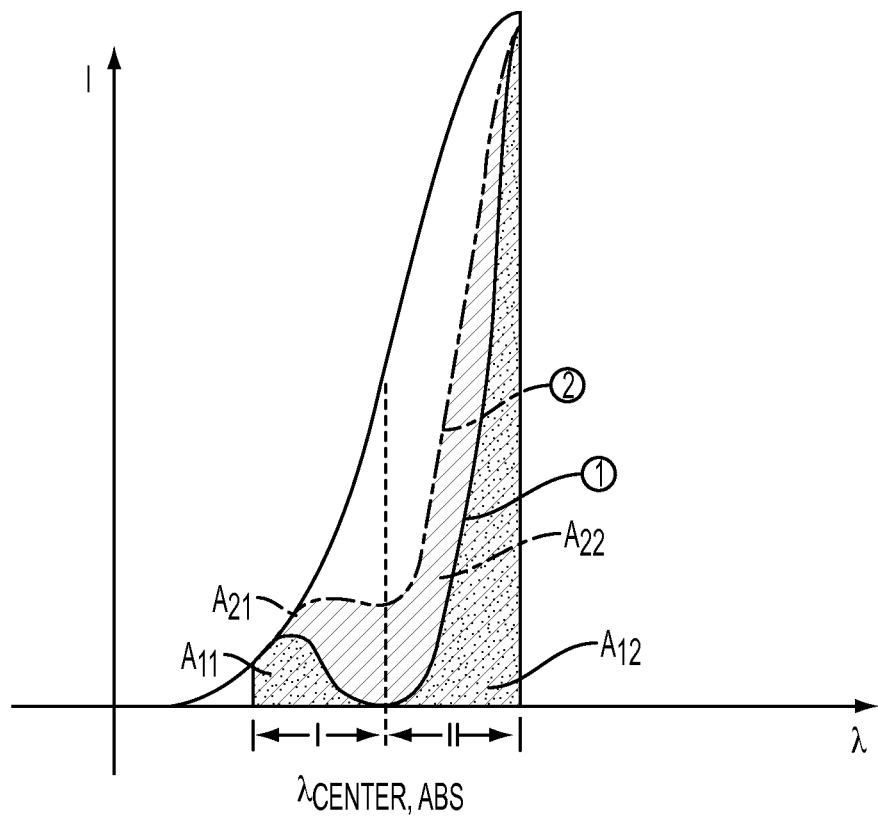
FIG. 15 shows another embodiment of a sensing scheme, where the wavelength centroid detector uses only a certain portion of the light source spectrum for determining changes to the centroid of the altered light source spectrum.

FIG. 15 shows another embodiment of a sensing scheme, where the wavelength centroid detector uses only a certain portion of the light source spectrum for determining changes to the centroid of the altered light source spectrum. If the detector design is tailored to the absorption band of the sensing layer, the linear variable filter transmission spectrum can be designed to be a bit broader than the absorption band of the sensor, as is indicated in FIG. 15 by the two sensing sections of the split diode labeled again as regions I and II, respectively. In FIG. 15, the characteristic absorption dip is visible with its center wavelength $\lambda_{center,Abs}$. Curve 1 represents a situation where no sensing agent is present. Curve 2 represents a situation where sensing agent is present. The wavelength range of the linear variable filter is indicated by the two detection regions of the split diode marked by regions I and II, respectively. The detection regions I and II are sensitive to the areas below curves 1 and 2, respectively, which are labeled $A_{11}$, $A_{12}$, $A_{21}$, and $A_{22}$.

In a situation where no sensing agent is present, a dip created by the absorption of the sensing layer can be observed in the transmission spectrum, shown in FIG. 15 and labeled as curve 1. The voltage signal of detecting region I is proportional to the area $A_{11}$ below curve 1, while the voltage signal of detection region II is proportional to the area $A_{12}$ below curve 1. Hence, the centroid of the light intensity can be measured/determined accurately using the photocurrent signals generated in detection regions I and II.

If the absorption coating of the sensing material is affected by a sensing agent, the absorption coating will change its absorption characteristics. This situation is depicted in FIG. 15 as curve 2. In particular, with increasing concentration of the sensing agent, the absorption dip will become smaller, as can be seen by comparing curve 2 and curve 1 in FIG. 15. The photocurrent generated in detection region I is still proportional to the left area under curve 2, now called $A_{21}$. In the same manner, the photocurrent signal in detection region II is still proportional to the right area under curve 2, now called $A_{21}$. As can be seen in FIG. 15, due to the monotonically rising/falling illumination spectrum, the normalized changes in area between $A_{11}$ to $A_{21}$ and $A_{12}$ to $A_{22}$ are not the same. Expressed mathematically, $$\frac{A_{12} - A_{11}}{A_{12} + A_{11}} \neq \frac{A_{22} - A_{21}}{A_{22} + A_{21}}.$$

Figure 16:
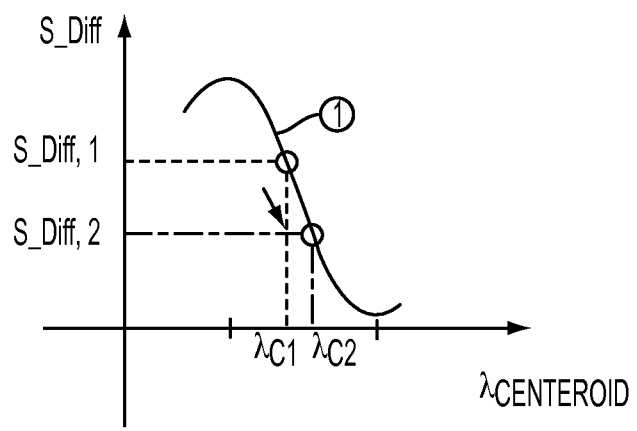
FIG. 16 illustrates the sensing characteristic and representative output signals of a wavelength centroid detector according to some embodiments.

FIG. 16 illustrates the sensing characteristic, labeled curve 1, and representative output signals S_Diff_1 and S_Diff_2 of a wavelength centroid detector according to the centroid wavelengths $\lambda_{C1}$ and $\lambda_{C2}$. Due to the detector characteristic shown in FIG. 16, indicated by curve 1, a change in the centroid in the wavelength $\lambda_C$ domain (e.g., from $\lambda_{C1}$ to $\lambda_{C2}$) results in a change in the detector output signal S_Diff. Thus, it is possible to detect a change in the sensor signal when the absorption of the sensing material changes and hence it is possible to read out the intensity encoded sensor using the disclosed sensing principle with high accuracy.

As previously discussed, overcharge and overdischarge of $Li_xC_6/Li_{1-x}CoO_2$ battery cells leads to considerable gas generation which may be ascribed to the decomposition reactions of the electrolyte. Even if the decomposition reactions differ for overcharge and over-discharge, chromatographic gas analysis showed that for both cases $CO_2$ showed the highest volume content within the detected gas volumes (>70%).

Thus, $CO_2$ is an attractive candidate for selective chemical sensing inside of Li-ion battery chemistries in order to monitor overcharging, over-discharging, leaking, cell abuse, cell formation and/or ageing mechanisms for commercial Li-ion cells. For example, $CO_2$ concentration in the 2-10% (volume fraction) range may indicate aging of the cell, while anything in excess of 10% may indicate overcharge/overdischarge. For alternative or future battery chemistries other free or dissolved gases may be better indicators.

Figure 17:
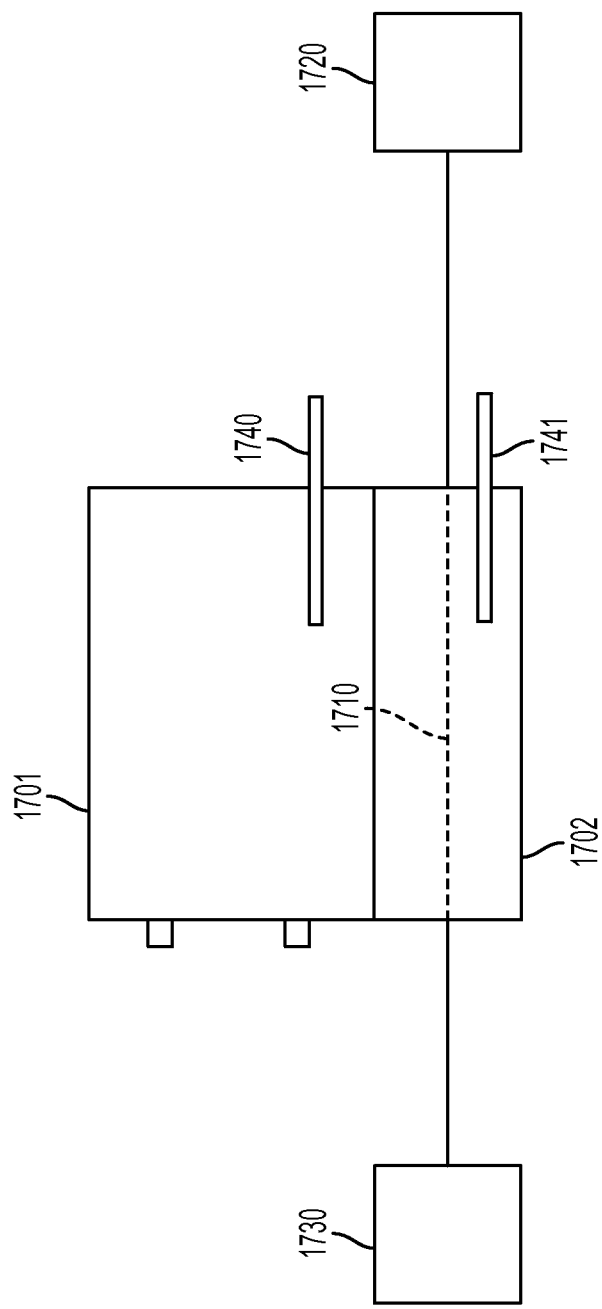
FIG. 17 shows the experimental test setup for in situ internal gas concentration measurements with fiber optics in accordance with some embodiments.

FIG. 17 shows the experimental test setup for in situ internal chemical measurements, e.g., free or dissolved gas concentration measurements, using internal fiber optic sensing. Initially, the fiber sensors 1710 have been implemented into the side pouch 1702 of the battery cell 1701. The side pouch is an excess part of the battery cell skin which is used for the collection of gaseous byproducts during the initial formation of the battery cell. It prevents a "swelling" of the cell stack during the formation cycles which would have a negative effect on the latter cell performance. After the formation step (and before shipping of the commercial battery cell to the customer) the side pouch is removed and the cell is re-sealed.

Input light for the fiber optic sensors 1710 was provided by a halogen light source 1720. The output light from the fiber optic sensors was analyzed by spectrometer 1730. Internal temperature of the cell 1701 was sensed by thermistor 1740 and side pouch temperature by thermistor 1741.

Figure 18:
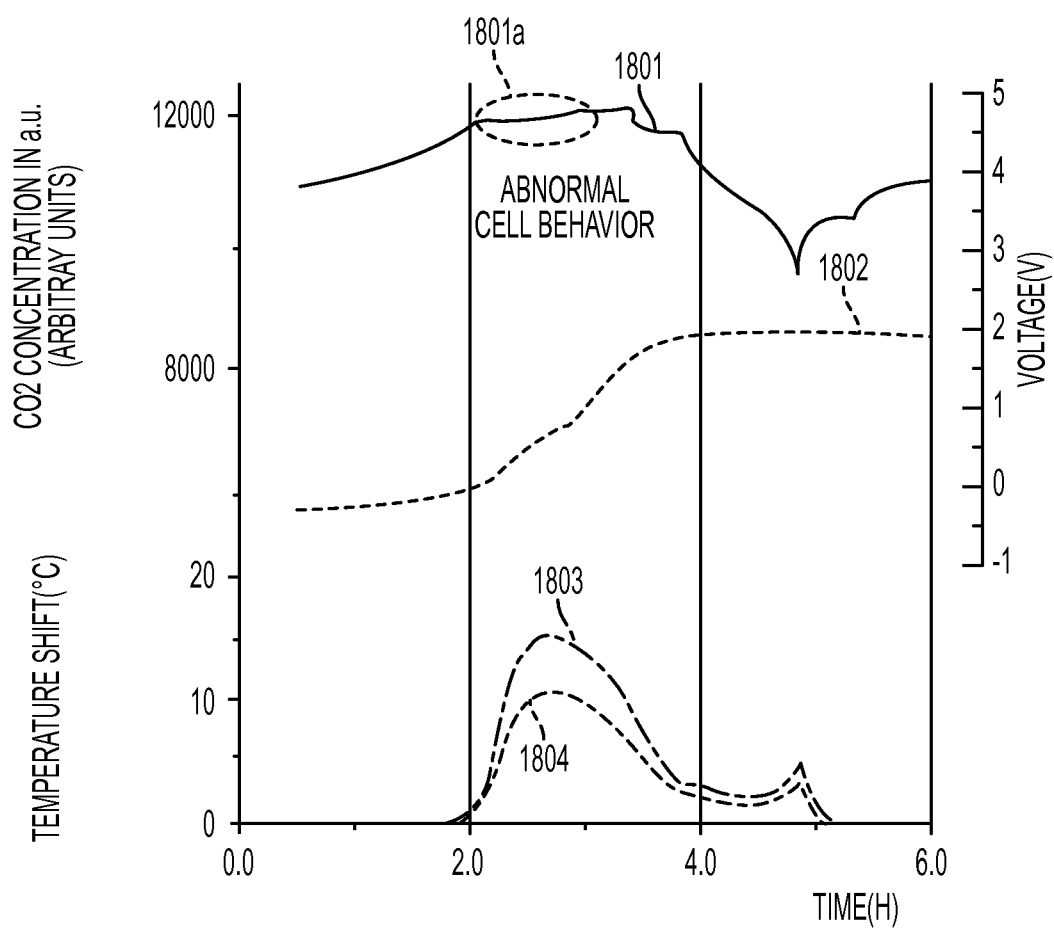
FIG. 18 shows results for gas evolution in a battery cell during cycling the battery into an overcharge regime.

As the overall goal of this experiment was to investigate the applicability of FO chemical sensing for battery environments in order to detect potential hazardous conditions and ageing effects, a relative aggressive overcharge cycle has been chosen as it is known to cause significant gas generation in Li-ion batteries. FIG. 18 shows results for gas evolution in a battery cell during cycling the battery into an overcharge regime. Curve 1801 is the cell voltage; curve 1802 is the normalized gas sensor signal; curve 1803 is the internal cell temperature; and curve 1804 is the temperature of the side pouch close to the location of the sensor.

During the charge period, the cell voltage 1801 exceeds the regular maximum voltage of 4.4V~1.9 h. The voltage experiences then significant variations at t~2.1 h, marked by a dashed circle 1801a. The cell voltage 1801 decreased temporarily during the charge event before reaching the cutoff voltage of 4.7 V, indicating variations in the internal resistance of the cell and leading to a voltage "dip" in the charge curve. This abnormal cell behavior has been observed also for other cells and is often accompanied by a significant temperature increase of $\Delta T=15$ C on the cell skin. Operating the cell in overcharge conditions correlates also with a considerable increase in the $CO_2$ sensor signal during overcharge for an extended timeframe of 1.5 h.

Overall, the sensor signal increases are always delayed with respect to the overcharge condition (V>4.4 V). Without being bound by any particular theory, this could have multiple reasons. First, it is not known at which precise cell voltage above the nominal upper level of 4.4 V electrolyte decomposition effects set in and gas evolution starts to occur. Second, a certain time delay due to gas diffusion processes from the point of origin to the chemical sensitive fiber in the side pouch of the battery cell should be taken into account. This delay can be mitigated by an implementation closer to the active material given that the sensing fiber stability can be adapted to the aggressive cell chemistry. For completeness, the time constant of the FO chemical sensor has to be taken into account. However, compared to the rise time of the signals observed in this study, sensing time constants within seconds can be neglected.

Evaluating the measured chemical sensor signals, gas evolution could clearly be detected during multiple overcharge events. Besides $CO_2$, other gaseous species are generated during the overcharge events but cross-sensitivities with gases known to be generated during electrolyte decomposing are not expected for the sensors described herein.

Systems, devices, or methods disclosed herein may include one or more of the features, structures, methods, or combinations thereof described herein. For example, a device or method may be implemented to include one or more of the features and/or processes described herein. It is intended that such device or method need not include all of the features and/or processes described herein, but may be implemented to include selected features and/or processes that provide useful structures and/or functionality.

In the above detailed description, numeric values and ranges are provided for various aspects of the implementations described. These values and ranges are to be treated as examples only, and are not intended to limit the scope of the claims. For example, embodiments described in this disclosure can be practiced throughout the disclosed numerical ranges. In addition, a number of materials are identified as suitable for various implementations. These materials are to be treated as exemplary, and are not intended to limit the scope of the claims.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. A system, comprising:
   one or more fiber optic sensors configured to be disposed within an electrochemical battery, each fiber optic sensor configured to receive input light and to provide output light that varies based on the input light and an amount of free or dissolved gas present within the battery; a light source configured to provide the input light to the fiber optic sensors;
   a detector configured to detect the output light and to generate an electrical detector signal in response to the output light; and
   battery management circuitry configured to determine that the battery is in a first battery state based at least in part on the detector signal indicating that the amount of free or dissolved gas is at or above a first threshold and to determine that the battery is in a second battery state based at least in part on the detector signal indicating that the amount of free or dissolved gas is at or above a second threshold different from the first threshold.

2. The system of claim 1, further comprising charging circuitry configured to charge the battery, wherein the battery management circuitry is configured to determine a state of charge of the battery and to control the charging circuitry based on the state of charge.

3. The system of claim 1, further comprising load management circuitry coupled to a load, wherein battery management circuitry is configured to determine a state of charge of the battery and to perform one or more of decoupling the load from the battery, coupling the load to the battery, reducing the load, and increasing the load based on the state of charge.

4. The system of claim 1, wherein the gas comprises $CO_2$.

5. The system of claim 1, wherein the gas comprises at least one of $O_2$ and $CH_4$.

6. The system of claim 1, wherein:
a first fiber optic sensor is sensitive to $CO_2$; and
a second fiber optic sensor is sensitive to a second gas.

7. The system of claim 6, wherein the second gas is a hydrocarbon gas.

8. The system of claim 7, wherein the hydrocarbon gas comprises at least one of $C_3H_8$, $C_2H_6$, and $CH_4$.

9. The system of claim 6, wherein the second gas comprises one or more of $O_2$, HF, CO, and $H_2$.

10. The system of claim 1, wherein the battery management circuitry is configured to detect abnormal gas generation based on comparison of the detector signal to a threshold value.

11. The system of claim 1, wherein the battery management circuitry is configured to detect abnormal gas generation based on a rate of change of the detector signal.

12. The system of claim 1, wherein the battery management circuitry is configured to detect abnormal gas generation within the battery based on a mathematical combination of a present detector signal value and a rate of change of the detector signal.

13. The system of claim 1, wherein the battery management circuitry is configured to discriminate between one or more of a nominally charged state, an overcharged state and an overdischarged state of the battery based on the detector signal.

14. The system of claim 1, wherein:
the one or more fiber optic sensors comprises multiple fiber optic sensors respectively configured to sense multiple gases present within the battery;
the detector comprises multiple detector elements providing multiple detector output signals, each detector element receiving output light from a particular fiber optic sensor; and
the battery management circuitry is configured to identify an abnormal reaction within the battery by comparing values of the multiple detector signals respectively to values in a set of threshold values associated with the abnormal reaction.

15. The system of claim 1, wherein the battery management circuitry is configured to start, stop and/or adaptively tune a rate of charging and/or discharging the battery based at least in part on the detector signal.

16. The system of claim 1, wherein the battery management circuitry is configured to use the detector signal to measure pH of the battery and to determine the state of the battery based at least in part on the measured pH.

17. The system of claim 1, wherein:
the gas comprises $CO_2$; and
the battery management circuitry is configured to compare the detector output signal to a $CO_2$ threshold value and to stop charging the battery if the detector output signal exceeds the $CO_2$ threshold.

18. The system of claim 1, wherein the state of the battery comprises a state of health of the battery.

19. The system of claim 1, further comprising at least one optical sensor disposed externally to the battery and configured to sense presence of an external gas that has leaked from the battery.

20. The system of claim 1, wherein the battery management circuitry is configured to predict battery failure based on the detector signal.

21. The system of claim 1, wherein the battery management circuitry is configured to predict thermal runaway based on the detector signal.

22. The method of claim 1, wherein:
determining the state of the battery comprises determining a state of charge of the battery; and
further comprising controlling at least one of charging and discharging the battery based on the state of charge.

23. A system, comprising:
one or more fiber optic sensors configured to be disposed within a case of an electrochemical battery, each fiber optic sensor configured to receive input light and to provide output light that varies based on an amount of a gas present within the battery;
a light source configured to provide the input light to the fiber optic sensors;
a detector configured to detect the output light and to generate an electrical detector output signal in response to the output light;
charging circuitry configured to charge the battery; and
battery management circuitry configured to determine that the battery is in a first battery state based at least in part of the detector signal indicating that the amount of gas is at or above a first threshold and to determine that the battery is in a second battery state based at least in part on the detector signal indicating that the amount of gas is at or above a second threshold different from the first threshold, the battery management circuitry further configured to provide feedback information to the charging circuit to control formation of the battery electrodes based at least in part on the detector signal.

24. The system of claim 23, wherein the battery management circuitry is configured to control formation of a solid-electrolyte interface (SEI) layer and/or avoid crack formation of the battery electrodes.

25. A method, comprising:
optically sensing within an electrochemical battery an amount of a free or dissolved gas present within the battery;
generating an electrical output signal in response to the sensed amount of gas;
determining that the battery is in a first battery state based at least in part on the detector signal indicating that the amount of free or dissolved gas is at or above a first threshold; and
determining that the battery is in a second battery state based at least in part on the detector signal indicating that the amount of free or dissolved gas is at or above a second threshold different from the first threshold.

26. A system, comprising:
one or more fiber optic sensors configured to be disposed within an electrochemical battery, each fiber optic sensor configured to receive input light and to provide output light that varies based on the input light and an amount of free or dissolved gas present within the battery; a light source configured to provide the input light to the fiber optic sensors; and
a detector configured to detect the output light and to generate an electrical detector signal in response to the output light, the electrical detector signal indicating that the battery is in a first battery state in response to a determination that the amount of free or dissolved gas is at or above a first threshold and indicating that the battery is in a second battery state in response to a determination that the amount of free or dissolved gas is at or above a second threshold different from the first threshold.

* * * * *